(12) United States Patent
Stroebel

(10) Patent No.: US 9,931,509 B2
(45) Date of Patent: Apr. 3, 2018

(54) FULLY INHIBITED DUAL CHAMBER PACING MODE

(75) Inventor: John C. Stroebel, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 67 days.

(21) Appl. No.: 13/412,120

(22) Filed: Mar. 5, 2012

(65) Prior Publication Data

US 2012/0165896 A1    Jun. 28, 2012

Related U.S. Application Data

(63) Continuation of application No. 11/681,827, filed on Mar. 5, 2007, now abandoned, which is a continuation of application No. 10/814,692, filed on Mar. 31, 2004, now Pat. No. 7,254,441, which is a continuation-in-part of application No. 10/246,816, filed on Sep. 17, 2002, now Pat. No. 7,130,683, which is a continuation-in-part of application No. 09/746,571, filed on Dec. 21, 2000, now Pat. No. 6,772,005.

(51) Int. Cl.
| | |
|---|---|
| *A61N 1/00* | (2006.01) |
| *A61N 1/368* | (2006.01) |
| *A61N 1/37* | (2006.01) |
| *A61N 1/362* | (2006.01) |

(52) U.S. Cl.
CPC .............. *A61N 1/368* (2013.01); *A61N 1/362* (2013.01); *A61N 1/3688* (2013.01); *A61N 1/37* (2013.01)

(58) Field of Classification Search
None
See application file for complete search history.

(56) References Cited

U.S. PATENT DOCUMENTS

| | | |
|---|---|---|
| 3,057,356 A | 10/1962 | Greatbatch |
| 3,253,596 A | 5/1966 | Keller |
| 3,478,746 A | 11/1969 | Greatbatch |
| 3,595,242 A | 7/1971 | Berkovits |
| 3,648,707 A | 3/1972 | Greatbatch |
| 3,747,604 A | 7/1973 | Berkovits |
| 4,312,355 A | 1/1982 | Funke |

(Continued)

FOREIGN PATENT DOCUMENTS

| | | |
|---|---|---|
| EP | 0363015 | 4/1990 |
| EP | 0448193 | 9/1991 |

(Continued)

OTHER PUBLICATIONS

"INTRINSIC™/INTRINSIC™ 30, 7288/7287 Reference Manual", May 24, 2004, 390 pages.

*Primary Examiner* — Michael Carey
*Assistant Examiner* — Elizabeth K So

(57) ABSTRACT

A pacing mode is provided, in one embodiment, that permits missed or skipped ventricular beats. The mode monitors a full cardiac cycle (A-A interval) for the presence of intrinsic ventricular activity. If ventricular activity is present, a flag is set that is valid for the next cardiac cycle. At the beginning of the next cardiac cycle, the device determines if the flag is present. So long as the flag is present, the device will not deliver a ventricular pacing pulse in that cycle, even if there is no intrinsic ventricular activity. If there is no flag present at the start of a given cardiac cycle, a ventricular pacing pulse is delivered and this ventricular activity sets a flag for the subsequent cardiac cycle.

11 Claims, 17 Drawing Sheets

(56) References Cited

U.S. PATENT DOCUMENTS

| | | |
|---|---|---|
| 4,386,610 A | 6/1983 | Leckrone |
| 4,412,541 A | 11/1983 | Schaldach et al. |
| 4,428,378 A | 1/1984 | Anderson et al. |
| 4,432,362 A | 2/1984 | Leckrone et al. |
| 4,476,868 A | 10/1984 | Thompson |
| 4,523,593 A | 6/1985 | Rueter et al. |
| 4,577,633 A | 3/1986 | Berkovits et al. |
| 4,587,970 A | 5/1986 | Holley et al. |
| 4,726,380 A | 2/1988 | Vollmann et al. |
| 4,727,877 A | 3/1988 | Kallok |
| 4,856,523 A | 8/1989 | Sholder et al. |
| 4,856,524 A | 8/1989 | Baker |
| 4,880,005 A | 11/1989 | Pless et al. |
| 4,890,617 A | 1/1990 | Markowitz et al. |
| 4,932,046 A | 6/1990 | Katz et al. |
| 4,941,471 A | 7/1990 | Mehra |
| 4,953,551 A | 9/1990 | Mehra et al. |
| 4,998,974 A | 3/1991 | Aker |
| 5,052,388 A | 10/1991 | Sivula et al. |
| 5,085,215 A | 2/1992 | Nappholz et al. |
| 5,097,832 A | 3/1992 | Buchanan |
| 5,117,824 A | 6/1992 | Keimel et al. |
| 5,133,350 A | 7/1992 | Duffin |
| 5,144,949 A | 9/1992 | Olson |
| 5,144,950 A | 9/1992 | Stoop et al. |
| 5,163,427 A | 11/1992 | Keimel |
| 5,188,105 A | 2/1993 | Keimel |
| 5,188,117 A | 2/1993 | Steinhaus et al. |
| 5,228,438 A | 7/1993 | Buchanan |
| 5,273,035 A | 12/1993 | Markowitz et al. |
| 5,292,340 A | 3/1994 | Crosby et al. |
| 5,318,594 A | 6/1994 | Limousin et al. |
| 5,326,623 A | 7/1994 | Yamakawa et al. |
| 5,334,220 A | 8/1994 | Sholder |
| 5,345,362 A | 9/1994 | Winkler |
| 5,372,607 A | 12/1994 | Stone et al. |
| 5,379,776 A | 1/1995 | Murphy et al. |
| 5,388,586 A | 2/1995 | Lee et al. |
| 5,417,714 A | 5/1995 | Levine et al. |
| 5,522,859 A | 6/1996 | Stroebel et al. |
| 5,540,725 A | 7/1996 | Bornzin et al. |
| 5,584,868 A | 12/1996 | Salo et al. |
| 5,591,214 A | 1/1997 | Lu |
| 5,626,623 A | 5/1997 | Kieval et al. |
| 5,643,326 A | 7/1997 | Weiner et al. |
| 5,645,569 A | 7/1997 | Ayers |
| 5,674,257 A | 10/1997 | Stroebel et al. |
| 5,683,426 A | 11/1997 | Greenhut et al. |
| 5,697,958 A | 12/1997 | Paul et al. |
| 5,716,382 A | 2/1998 | Snell |
| 5,725,561 A | 3/1998 | Stroebel et al. |
| 5,741,308 A | 4/1998 | Sholder et al. |
| 5,814,077 A | 9/1998 | Levine et al. |
| 5,836,974 A | 11/1998 | Christini et al. |
| 5,861,007 A | 1/1999 | Hess et al. |
| 5,873,895 A | 2/1999 | Sholder et al. |
| 5,893,882 A | 4/1999 | Peterson et al. |
| 5,954,755 A | 9/1999 | Casavant |
| 5,999,850 A | 12/1999 | Dawson et al. |
| 6,058,326 A | 5/2000 | Hess et al. |
| 6,122,546 A | 9/2000 | Levine et al. |
| 6,128,529 A | 10/2000 | Esler et al. |
| 6,128,534 A | 10/2000 | Park et al. |
| 6,141,586 A | 10/2000 | Mower |
| 6,157,859 A | 12/2000 | Alt |
| 6,169,918 B1 | 1/2001 | Haefner et al. |
| 6,198,968 B1 | 3/2001 | Prutchi et al. |
| 6,256,541 B1 | 7/2001 | Heil et al. |
| 6,321,115 B1 | 11/2001 | Mouchawar et al. |
| 6,397,105 B1 | 5/2002 | Bouhour et al. |
| 6,434,424 B1 | 8/2002 | Igel et al. |
| 6,477,416 B1 | 11/2002 | Florio et al. |
| 6,609,028 B2 | 8/2003 | Struble |
| 6,654,637 B2 | 11/2003 | Rouw et al. |
| 6,697,673 B1 | 2/2004 | Lu |
| 6,731,980 B1 | 5/2004 | Mouchawar et al. |
| 6,772,005 B2 | 8/2004 | Casavant et al. |
| 6,792,307 B1 | 9/2004 | Levine et al. |
| 6,871,097 B1 | 3/2005 | Strandberg |
| 6,873,875 B1 | 3/2005 | Gilkerson et al. |
| 6,904,315 B2 | 6/2005 | Panken et al. |
| 6,925,326 B1 | 8/2005 | Levine et al. |
| 6,978,175 B1 | 12/2005 | Florio et al. |
| 7,027,868 B2 | 4/2006 | Rueter et al. |
| 7,123,960 B2 | 10/2006 | Ding et al. |
| 7,130,683 B2 | 10/2006 | Casavant et al. |
| 7,218,965 B2 | 5/2007 | Casavant et al. |
| 7,245,966 B2 | 7/2007 | Betzold et al. |
| 7,248,924 B2 | 7/2007 | Casavant |
| 7,252,640 B2 | 8/2007 | Ni et al. |
| 7,254,441 B2 | 8/2007 | Stroebel |
| 7,283,872 B2 | 10/2007 | Boute et al. |
| 7,587,242 B2 | 9/2009 | Casvant et al. |
| 7,925,345 B2 | 4/2011 | Casavant et al. |
| 7,957,800 B2 | 6/2011 | Casavant et al. |
| 2002/0038482 A1 | 4/2002 | Mennicke et al. |
| 2002/0041700 A1 | 4/2002 | Therbaud |
| 2002/0082646 A1 | 6/2002 | Casavant et al. |
| 2002/0123760 A1 | 9/2002 | Amplatz |
| 2002/0128687 A1 | 9/2002 | Baker et al. |
| 2002/0138417 A1 | 9/2002 | Lawrence |
| 2003/0078627 A1 | 4/2003 | Casavant et al. |
| 2004/0010292 A1 | 1/2004 | Amblard et al. |
| 2004/0024694 A1 | 2/2004 | Lawrence et al. |
| 2004/0078321 A1 | 4/2004 | Lawrence |
| 2004/0117316 A1 | 6/2004 | Gillum |
| 2004/0260349 A1 | 12/2004 | Stroebel |
| 2005/0038482 A1 | 2/2005 | Yonce et al. |
| 2005/0055059 A1 | 3/2005 | Betzold et al. |
| 2005/0096708 A1 | 5/2005 | Seim et al. |
| 2005/0177197 A1 | 8/2005 | Betzold |
| 2005/0267539 A1 | 12/2005 | Betzold et al. |
| 2005/0273430 A1 | 12/2005 | Pliha |
| 2007/0203523 A1 | 8/2007 | Betzold |
| 2007/0213777 A1 | 9/2007 | Betzold et al. |

FOREIGN PATENT DOCUMENTS

| | | |
|---|---|---|
| EP | 0624386 | 11/1994 |
| EP | 0830877 | 3/1998 |
| EP | 1449562 | 8/2004 |
| WO | WO 95/32758 | 12/1995 |
| WO | 9910044 A1 | 3/1999 |
| WO | WO 02/051499 | 7/2002 |
| WO | WO 2005/097259 | 10/2005 |
| WO | WO 2005/113065 | 12/2005 |
| WO | WO 2006/079037 | 7/2006 |
| WO | WO 2006/079066 | 7/2006 |

FULLY INHIBITED DUAL CHAMBER PACING MODE

CROSS REFERENCE TO RELATED APPLICATIONS

This application is a continuation application of Ser. No. 11/681,827, filed Mar. 5, 2007 entitled "FULLY INHIBITED DUAL CHAMBER PACING MODE", which is a continuation application of Ser. No. 10/814,692, filed Mar. 31, 2004, now U.S. Pat. No. 7,254,441, issued Aug. 7, 2007 entitled "FULLY INHIBITED DUAL CHAMBER PACING MODE", which is a continuation-in-part of application Ser. No. 10/246,816, filed Sep. 17, 2002, now U.S. Pat. No. 7,130,683, issued Oct. 31, 2006 entitled "PREFERRED ADI/R: A PERMANENT PACING MODE TO ELIMINATE VENTRICULAR PACING WHILE MAINTAINING BACKUP SUPPORT", which is a continuation-in-part of application Ser. No. 09/746,571, filed Dec. 21, 2000, now U.S. Pat. No. 6,772,005, issued Aug. 3, 2004 entitled "PREFERRED ADI/R: A PERMANENT PACING MODE TO ELIMINATE VENTRICULAR PACING WHILE MAINTAINING BACKUP SUPPORT", all of which are herein incorporated by reference in their entireties.

BACKGROUND OF THE INVENTION

The present invention relates to implantable medical devices. More particularly, the present invention relates to implantable pacemakers, cardioverters, and defibrillators.

DESCRIPTION OF THE RELATED ART

There are a variety of implantable medical devices (IMD) that are used to monitor cardiac conditions and deliver therapy when appropriate. Pacemakers and defibrillators, alone or in combination, typically sense events relating to the cardiac cycle and deliver electrical stimulation to affect a desired result. Pacemakers sense cardiac cycles and deliver lower energy pulses at predetermined intervals to depolarize cardiac tissue in the atria, ventricles, or both in order to maintain or control the cardiac rhythm. Defibrillators sense fibrillation of the atria or ventricles and deliver a higher energy stimulation in order to defibrillate the heart and reinstate a sinus rhythm. Commonly, both types of functions are included in a single device referred to as an implantable cardioverter/defibrillator (ICD).

The cardiac cycle begins with a depolarization of the atria starting at the SA node, represented by a P-wave on an EKG or EGM. As the depolarization wave travels through the atria, it encounters the AV node, experiences a delay (AV interval) and eventually depolarizes the ventricles, which appears as a QRS complex on the EKG or EGM. Subsequent repolarization of the ventricles appears as a T-wave. At its most basic level, the cardiac cycle consists of an atrial (A) event or P wave, followed by a ventricular event (V) or R-wave. Such events are either intrinsic or paced. Thus, over time multiple cycles simply produce a repetitive A-V-A-V pattern.

For purposes of timing, this overview of the cardiac cycle results in a few relatively simple options. An A-A interval is effectively a complete cycle and represents the interval or time between subsequent atrial events. Similarly, the V-V interval is the time between subsequent ventricular events and also represents a complete cycle. The AV interval is the time between the atrial event and the ventricular event and the VA interval is the time between the ventricular event and the subsequent atrial event.

While very basic and certainly well known, these various intervals represent the framework used for ICD timing. For example, in a patient having complete AV block, depolarization of the atria may occur normally, however the depolarization wave fails to reach the ventricles. Thus, the ventricles depolarize independently of the atria at their own intrinsic rate, which is usually slower than the atrial rate. An ICD configured to pace the ventricles will sense the atrial depolarization. Thus, when A is sensed, an AV escape interval timer is started. At the completion of the AV escape interval, the pacing pulse is delivered.

The particular rules, timers, triggers and operations that the ICD will follow are defined by modes of operation. The NBG Pacemaker code (NASPE/BPEG Generic Pacemaker Code) is typically used to generically indicate the functionality of a given mode or device. The code includes 5 designations. The first indicates the chamber paced, the second the chamber sensed, the third the response to sensing, the fourth relates to programmability and more typically rate responsiveness, and the fifth is related to anti-tachy functions and is often not included. Thus, a VVI/R pacemaker paces in the ventricle, senses in the ventricle, inhibits a pacing pulse based on a sensed event and is rate responsive. As mentioned, this code generically indicates the mode and various manufacturers may implement such modes in different manners and with different specific parameters.

ICD's often have the ability to automatically switch from one mode to another, based on sensed conditions. Thus, a single chamber pacemaker having a single lead may only function in single chamber modes (e.g., VVI). More complex ICD's having, for example, dual, triple or quadruple chambered pacing/sensing will be able to function in any of the available modes, including the single chamber modes.

As long as that device is in a given mode, it will function according to the rules of that mode regardless of other capabilities. For example, a device truly in a VVI mode will not respond to atrial events, atrial arrhythmia's etc. If such atrial events are detected while in VVI and they require a response, the device will mode switch to an appropriate mode. With the generic nature of these codes and the ever-changing capabilities of ICD's, the codes are often used to indicate the closest approximation for a given mode. Thus, in a given context for a particular device, a specific mode may have capabilities that go beyond the code designations. However, every mode will have a set of rules and the device will not violate those rules when operating in that mode.

SUMMARY OF THE INVENTION

The present invention, in one embodiment, is a mode for an implantable medical device, for example a pacemaker or ICD.

The present invention includes a method of selectively providing cardiac pacing with an implantable medical device. The method includes setting a flag during a given cardiac cycle in response to ventricular activity and precluding a ventricular pacing pulse during a current cardiac cycle if the flag is present at the onset of the current cardiac cycle.

In one embodiment, the present invention is an implantable medical device comprising means for sensing cardiac depolarizations. The implantable medical device also includes means for pacing and means for controlling the means for pacing according to a selected mode, wherein one selectable mode is a fully inhibited DDI (FIDDI) mode.

In another embodiment, the present invention is an implantable medical device comprising means for sensing cardiac depolarizations and means for pacing according to a selectable mode. The implantable medical device also includes means for mode switching to an atrial based pacing mode upon the sensing of ventricular activity in a given cardiac cycle and means for mode switching from the atrial based pacing mode to a dual chamber mode at the completion of the given cardiac cycle, wherein the dual chamber mode includes a first set of parameters that are implemented for a first cardiac cycle while operating in the dual chamber mode such that the implemented parameters preclude the delivery of a ventricular pacing pulse during the first cardiac cycle and a second set of parameters implemented in a second consecutive cardiac cycle while operating in the dual chamber mode such that ventricular pacing is delivered unless inhibited.

In another embodiment, the present invention is an implantable medical device comprising a controller and a ventricular lead operably coupled to the controller and configured to deliver ventricular pacing pulses and sense ventricular depolarizations. The implantable medical device also includes an atrial lead operable coupled to the controller and configured to deliver atrial pacing pulses and sense atrial depolarizations and a memory including a plurality of algorithms defining pacing modalities selectable by the controller, wherein one of the pacing modalities is fully inhibited DDI.

In another embodiment, the present invention is a computer readable medium including instructions that define a pacing mode that when implemented on an implantable medical device cause the implantable medical device to set a flag in response to ventricular activity occurring in a current cardiac cycle, wherein the flag is valid for a subsequent cardiac cycle. In addition, the IDM determines if a flag is present at the start of a given cardiac cycle, initiates an atrial escape interval if the flag is present at the start of the given cardiac cycle, and initiates an AV interval if no flag is present at the start of the given cardiac cycle. In addition, the IMD delivers a ventricular pacing pulse at the completion of the AV interval and initiates a VA interval at the completion of the AV interval.

The present invention also include a method of operating an implantable medical device in a mode, the method comprising setting a flag during a first cardiac cycle if a pre-established criteria is met during the first cardiac cycle. The method also includes determining whether the flag has been set at the initiation of a second cardiac cycle that is consecutive to the first cardiac cycle, acting in a first manner during the second cardiac cycle and while remaining in the mode if the flag has been set and acting in a second manner during the second cardiac cycle and while remaining in the mode if the flag has not been set.

In another embodiment, the present invention is an implantable medical device (IMD) having mode-switching capability for delivering pacing therapy in a selected mode, comprising an atrial lead, a ventricular lead, and a memory. The IMD also includes a processing module in electronic communication with the ventricular lead and the memory wherein the processing module sets a flag in the memory during a first cardiac cycle if a pre-established criteria is sensed or delivered via the ventricular lead during the first cardiac cycle and determines whether the flag has been set at the initiation of a second cardiac cycle that is consecutive to the first cardiac cycle. Also included is a controller that initiates an atrial escape interval and precludes ventricular pacing during the second cardiac cycle and while remaining in the selected mode if the flag has been set and the controller initiates an AV interval and a ventricular pacing pulse during the second cardiac cycle and while remaining in the selected mode if the flag has not been set.

The present invention also includes a method of selectively providing cardiac pacing with an implantable medical device. The method includes setting a flag during a given cardiac cycle in response to ventricular activity and delivering a ventricular pacing pulse during a current cardiac cycle only if a flag is absent at the onset of the given cardiac cycle.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

Figure 1:
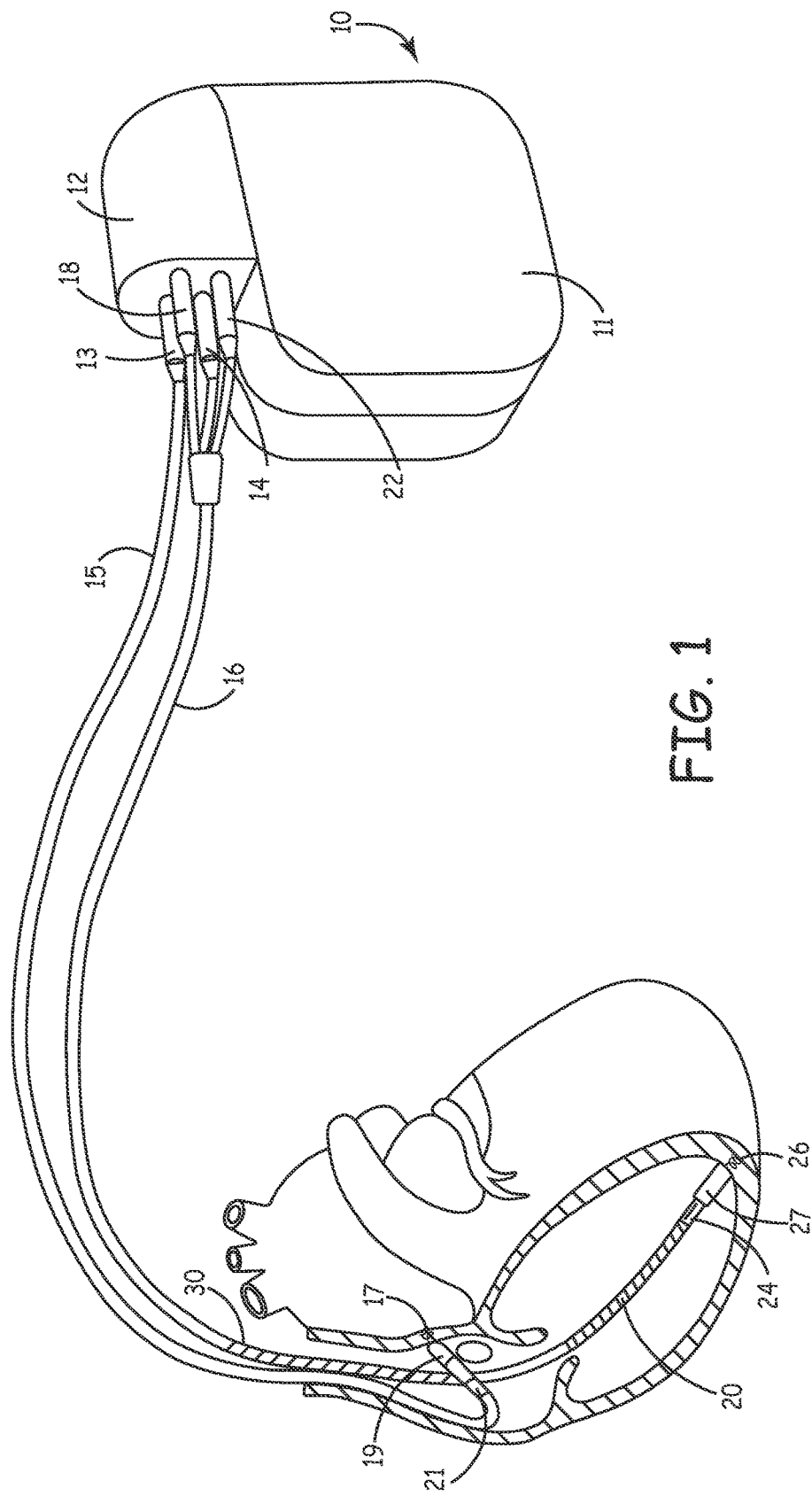
FIG. 1 is an illustration of an ICD system according to the present invention.

Referring now to FIG. 1, there are illustrated an ICD 10 and leads 15 and 16, making up the system. ICD 10 is an implantable cardioverter defibrillator or could also be an implantable pulse generator. It should be appreciated that such a device may include pacing, defibrillation, cardioversion, and/or other therapies alone or in any combination. The leads shown are illustrative, it being noted that other specific forms of leads are within the scope of this invention. Ventricular lead 16 as illustrated has, located adjacent to the distal end, an extendable helix electrode 26 and a ring electrode 24, the helix electrode being mounted retractably within an insulative head 27. Electrodes 24 and 26 are used for bipolar ventricular pacing and for bipolar sensing of ventricular depolarizations. While electrodes 24 and 26 may be used for bipolar pacing and sensing, electrode 26 may be used in conjunction with the surface of device casing 10, which surface acts as a common or indifferent electrode in what is termed unipolar operation. Ventricular lead 16 also carries a coil electrode 20, sometimes referred to as the RV (right ventricular) coil, for delivering defibrillation and/or cardioversion pulses. Coil electrode 20 is positioned on lead 16 so that when the distal tip is at the apex of the ventricle, coil 20 is positioned in the right ventricle. Lead 16 may also carry, optionally, an SVC coil 30, which can be used for applying cardioversion pulses. Lead 16 carries respective concentric coil conductors (not shown), separated from one another by appropriate means such as tubular insulative sheaths and running the length of the lead for making electrical connection between the ICD device 10 and respective ones of electrodes 20, 24, 26 and 30.

Atrial lead 15 as illustrated includes an extendable helix electrode 17 and a ring electrode 21, the helix electrode being mounted retractably within an insulative head 19. Electrodes 17 and 21 are used for bipolar atrial pacing and for sensing atrial depolarizations. While electrodes 17 and 21 may be used for bipolar pacing and sensing, electrode 17 may be used in conjunction with the surface of device casing 10, which surface acts as a common or indifferent electrode in what is termed unipolar operation. Note that, in this example, atrial lead 15 is not equipped with coils for use in the sensing and delivery of cardioversion of defibrillation pulses. This is not meant to preclude the inclusion of such applications that may be used advantageously with the present invention.

An ICD device 10, is shown in combination with atrial and ventricular leads, with the lead connector assembly 13, 14, 18, and 22 being inserted into the connector block 12 of the device 10. A specific example of a defibrillation pulse generator that may be used in conjunction with the present ventricular lead is disclosed in U.S. Pat. No. 4,953,551. Other ICD type units can be used; reference is made to U.S. Pat. Nos. 5,163,427 and 5,188,105 as disclosing illustrative forms of apparatus for delivering cardioversion and defibrillation pulses. As used herein, the term "ICD type" device refers to any device that can apply both pacing therapy and shock therapy for controlling arrhythmias.

Figure 2:
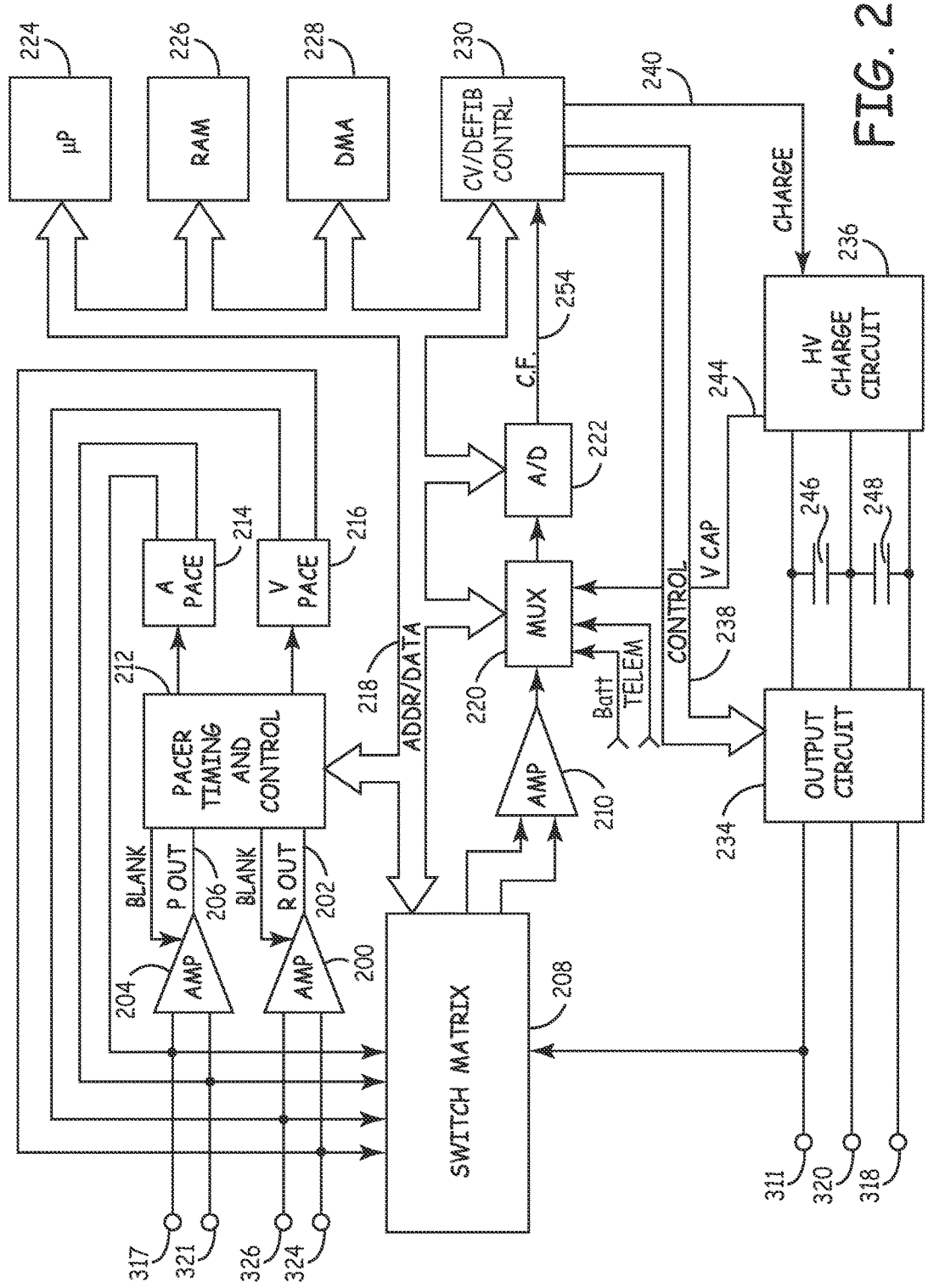
FIG. 2 is a block, functional diagram of ICD adapted to carry out the features of the present invention.

FIG. 2 is a functional schematic diagram of an implantable pacemaker/cardioverter/defibrillator in which the present invention may usefully be practiced. This diagram should be taken as exemplary of the type of device in which the invention may be embodied, and not as limiting, as it is believed that the invention may usefully be practiced in a wide variety of device implementations, including devices providing therapies for treating atrial arrhythmias instead of or in addition to ventricular arrhythmias, cardioverters and defibrillators which do not provide anti-tachycardia pacing therapies, anti-tachycardia pacers which do not provide cardioversion or defibrillation, and devices which deliver different forms of anti-arrhythmia therapies such as nerve stimulation or drug administration.

The device is provided with a lead system including electrodes, which may be as illustrated in FIG. 1. Alternate lead systems may of course be substituted. If the electrode configuration of FIG. 1 is employed, the correspondence to the illustrated electrodes is as follows. Electrode 311 corresponds to electrode 16, and is the uninsulated portion of the housing of the implantable pacemaker/cardioverter/defibrillator. Electrode 320 corresponds to electrode 20 and is a defibrillation electrode located in the right ventricle. Electrode 318 corresponds to electrode 30 and is a defibrillation electrode located in the superior vena cava. Electrodes 324 and 326 correspond to electrodes 24 and 26, and are used for sensing and pacing in the ventricle. Electrodes 317 and 321 correspond to electrodes 17 and 21 and are used for pacing and sensing in the atrium.

Electrodes 311, 318 and 320 are coupled to high voltage output circuit 234. Electrodes 324 and 326 are located on or in the ventricle and are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 324 and 326 exceeds the present sensing threshold.

Electrodes 317 and 321 are located on or in the atrium and are coupled to the P-wave amplifier 204, which preferably also takes the form of an automatic gain controlled amplifier providing an adjustable sensing threshold as a function of the measured P-wave amplitude. A signal is generated on P-out line 206 whenever the signal sensed between electrodes 317 and 321 exceeds the present sensing threshold. The general operation of the R-wave and P-wave amplifiers 200 and 204 may correspond to that disclosed in U.S. Pat. No. 5,117,824, by Keimel et al., issued Jun. 2, 1992, for an Apparatus for Monitoring Electrical Physiologic Signals, incorporated herein by reference in its entirety.

Switch matrix 208 is used to select which of the available electrodes are coupled to wide band (0.5-200 Hz) amplifier 210 for use in signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by ND converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal-processing methodologies known to the art.

The remainder of the circuitry is dedicated to the provision of cardiac pacing, cardioversion and defibrillation therapies, and, for purposes of the present invention may correspond to circuitry known in the prior art. An exemplary apparatus is disclosed of accomplishing pacing, cardioversion and defibrillation functions follows. The pacer timing/control circuitry 212 includes programmable digital counters which control the basic time intervals associated with DDD, VVI, DVI, VDD, AAI, DDI and other modes of single and dual chamber pacing well known to the art. Circuitry 212 also controls escape intervals associated with anti-tachyarrhythmia pacing in both the atrium and the ventricle, employing any anti-tachyarrhythmia pacing therapies known to the art.

Intervals defined by pacing circuitry 212 include atrial and ventricular pacing escape intervals, the refractory periods during which sensed P-waves and R-waves will not restart the escape pacing interval timing. The durations of these intervals are determined by microprocessor 224, in response to stored data in memory 226 and are communicated to the pacing circuitry 212 via address/data bus 218. Pacer circuitry 212 also determines the amplitudes and pulse widths of the cardiac pacing pulses under control of microprocessor 224.

During pacing, the escape interval timers within pacer timing/control circuitry 212 are reset upon sensing of R-waves and P-waves as indicated by signals on lines 202 and 206, and in accordance with the selected mode of pacing on timeout trigger generation of pacing pulses by pacer output circuitry 214 and 216, which are coupled to electrodes 317, 321, 324 and 326. The escape interval timers are also reset on generation of pacing pulses, and thereby control the basic timing of cardiac pacing functions, including anti-tachyarrhythmia pacing. The durations of the intervals defined by the escape interval timers are determined by microprocessor 224, via data/address bus 218. The value of the count present in the escape interval timers when reset by sensed R-waves and P-waves may be used to measure the durations of R-R intervals, P-P intervals, P-R intervals, and R-P intervals, which measurements are stored in memory 226 and used in conjunction with the present invention to diagnose the occurrence of a variety of tachyarrhythmias, as discussed in more detail below.

Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. A portion of the memory 226 may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

The arrhythmia detection method of the ICD may include prior art tachyarrhythmia detection algorithms. As described below, the entire ventricular arrhythmia detection methodology of presently available Medtronic pacemaker/cardioverter/defibrillators is employed as part of the arrhythmia detection and classification method according to the disclosed preferred embodiment of the invention. However, any of the various arrhythmia detection methodologies known to the art, as discussed in the Background of the Invention section above might also be usefully employed in alternative embodiments of the ICD.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing and control circuitry 212, to control the operation of the escape interval timers therein and to define refractory periods during which detection of R-waves and P-waves is ineffective to restart the escape interval timers. Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 7,726,380, issued to Vollmann et al. on Feb. 23, 1988 and U.S. Pat. No. 4,587,970, issued to Holley et al. on May 13, 1986, all of which are incorporated herein by reference in their entireties may also be used.

In the event that generation of a cardioversion or defibrillation pulse is required, microprocessor 224 employs the escape interval timer to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240 242. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization.

One embodiment of an appropriate system for delivery and synchronization of ventricular cardioversion and defibrillation pulses and for controlling the timing functions related to them is disclosed in more detail in commonly assigned U.S. Pat. No. 5,188,105 by Keimel, issued Feb. 23, 1993, and incorporated herein by reference in its entirety. If atrial defibrillation capabilities are included in the device, appropriate systems for delivery and synchronization of atrial cardioversion and defibrillation pulses and for controlling the timing functions related to them may be found in PCT Pat. Application No. WO92/18198 by Adams et al., published Oct. 29, 1992, and in U.S. Pat. No. 4,316,472 by Mirowski et al., issued Feb. 23, 1982, both incorporated herein by reference in their entireties.

However, any known cardioversion or defibrillation pulse control circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al, cited above, and in U.S. Pat. No. 4,375,817, issued to Engle et al, all incorporated herein by reference in their entireties may also be employed.

In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse. An example of output circuitry for delivery of biphasic pulse regimens may be found in the above cited patent issued to Mehra and in U.S. Pat. No. 4,727,877, incorporated by reference in its entirety.

An example of circuitry which may be used to control delivery of monophasic pulses is set forth in commonly assigned U.S. Pat. No. 5,163,427, by Keimel, issued Nov. 17, 1992, also incorporated herein by reference in its entirety. However, output control circuitry as disclosed in U.S. Pat. No. 4,953,551, issued to Mehra et al. on Sep. 4, 1990 or U.S. Pat. No. 4,800,883, issued to Winstrom on Jan. 31, 1989 both incorporated herein by reference in their entireties, may also be used in conjunction with a device embodying the present invention for delivery of biphasic pulses.

In modern implantable cardioverter/defibrillators, the physician, from a menu of therapies that are typically provided, programs the specific therapies into the device. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher energy cardioversion pulse may be selected for subsequent delivery. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion pulses if the rate of the detected tachycardia is below a preset threshold. The references cited above in conjunction with descriptions of prior art tachycardia detection and treatment therapies are applicable here as well.

In the event that fibrillation is identified, the typical therapy will be the delivery of a high amplitude defibrillation pulse, typically in excess of 5 joules. Lower energy levels may be employed for cardioversion. As in the case of currently available ICD's, and as discussed in the above-cited references, it is envisioned that the amplitude of the defibrillation pulse may be incremented in response to failure of an initial pulse or pulses to terminate fibrillation. Prior art patents illustrating such pre-set therapy menus of anti-tachyarrhythmia therapies include the above-cited U.S. Pat. No. 4,830,006, issued to Haluska et al., U.S. Pat. No. 4,727,380, issued to Vollmann et al. and U.S. Pat. No. 4,587,970, issued to Holley et al.

Figure 3:
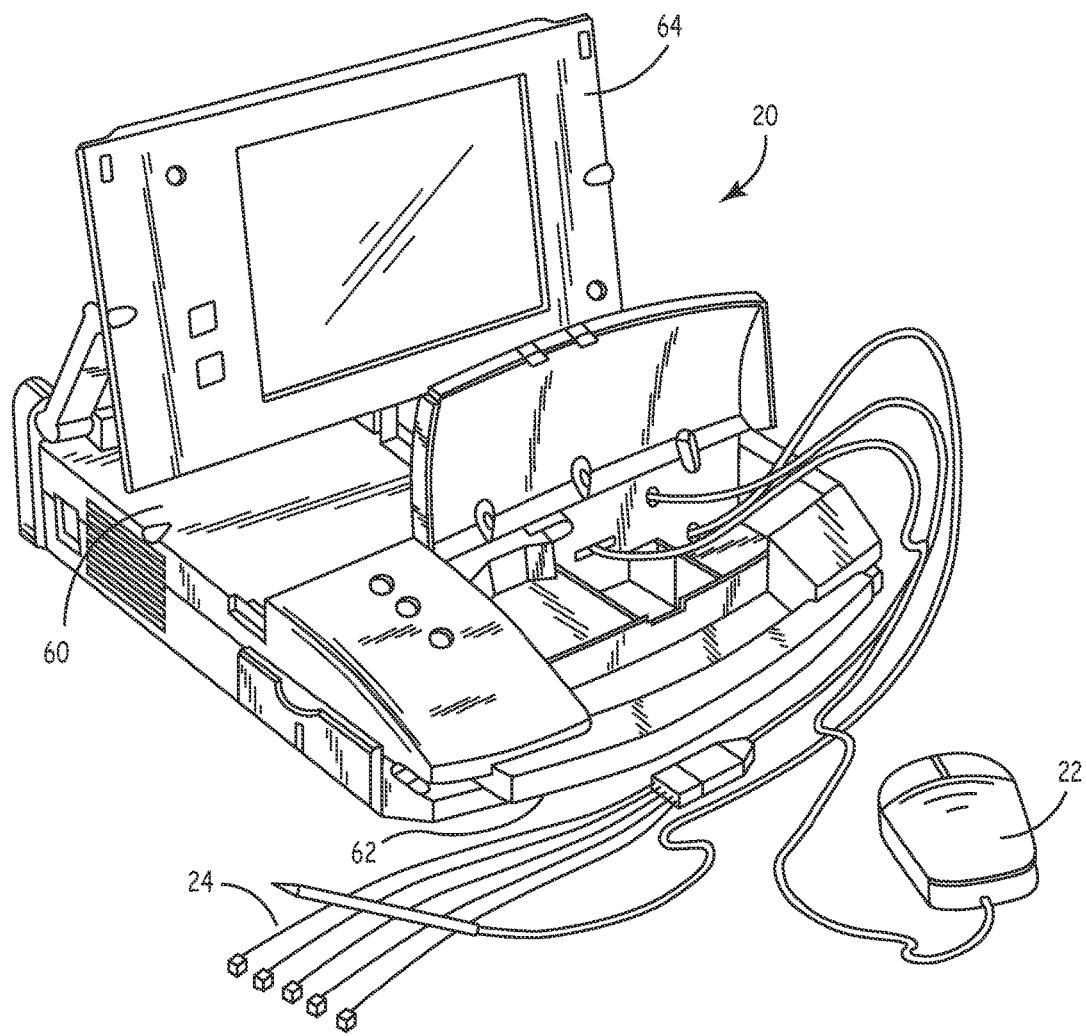
FIG. 3 is a perspective view of the external programming unit of FIG. 1.

FIG. 3 is a perspective view of programming unit program 20 in accordance with the present invention. Internally, programmer 20 includes a processing unit (not shown in the Figure) that in accordance with the presently disclosed invention is a personal computer type motherboard, e.g., a computer motherboard including an Intel Pentium 3 microprocessor and related circuitry such as digital memory. The details of design and operation of the programmer's computer system will not be set forth in detail in the present disclosure, as it is believed that such details are well-known to those of ordinary skill in the art.

Referring to FIG. 3, programmer 20 comprises an outer housing 60, which is preferably made of thermal plastic or another suitably rugged yet relatively lightweight material. A carrying handle, designated generally as 62 in FIG. 2, is integrally formed into the front of housing 60. With handle 62, programmer 20 can be carried like a briefcase.

An articulating display screen 64 is disposed on the upper surface of housing 60. Display screen 64 folds down into a closed position (not shown) when programmer 20 is not in use, thereby reducing the size of programmer 20 and protecting the display surface of display 64 during transportation and storage thereof.

A floppy disk drive is disposed within housing 60 and is accessible via a disk insertion slot (not shown). A hard disk drive is also disposed within housing 60, and it is contemplated that a hard disk drive activity indicator, (e.g., an LED, not shown) could be provided to give a visible indication of hard disk activation.

As would be appreciated by those of ordinary skill in the art, it is often desirable to provide a means for determining the status of the patient's conduction system, heart rhythm, electrical activation and a number of other parameters. Normally, programmer 20 is equipped with external ECG leads 24.

In accordance with the present invention, programmer 20 is equipped with an internal printer (not shown) so that a hard copy of a patient's ECG or of graphics displayed on the programmer's display screen 64 can be generated. Several types of printers, such as the AR-100 printer available from General Scanning Co., are known and commercially available.

In the perspective view of FIG. 3, programmer 20 is shown with articulating display screen 64 having been lifted up into one of a plurality of possible open positions such that the display area thereof is visible to a user situated in front of programmer 20. Articulating display screen is preferably of the LCD or electro-luminescent type, characterized by being relatively thin as compared, for example, a cathode ray tube (CRT) or the like.

As would be appreciated by those of ordinary skill in the art, display screen 64 is operatively coupled to the computer circuitry disposed within housing 60 and is adapted to provide a visual display of graphics and/or data under control of the internal computer.

Programmer 20 described herein with reference to FIG. 2 is described in more detail in U.S. Pat. No. 5,345,362 issued to Thomas J. Winkler, entitled Portable Computer Apparatus With Articulating Display Panel, which patent is hereby incorporated herein by reference in its entirety. The Medtronic Model 9790 programmer is the implantable device-programming unit with which the present invention may be advantageously practiced.

As mentioned, ICD 10 may include various cardiac rhythm management capabilities such as sensing and pacing. As such, the ICD 10 operates under a given set of rules defined by the mode that the ICD 10 is in at a given time. The mode selected will depend upon the physiologic needs of the patient, which could vary over time. Thus, the ICD 10 may selectively switch between modes to best address such conditions.

Figure 4:
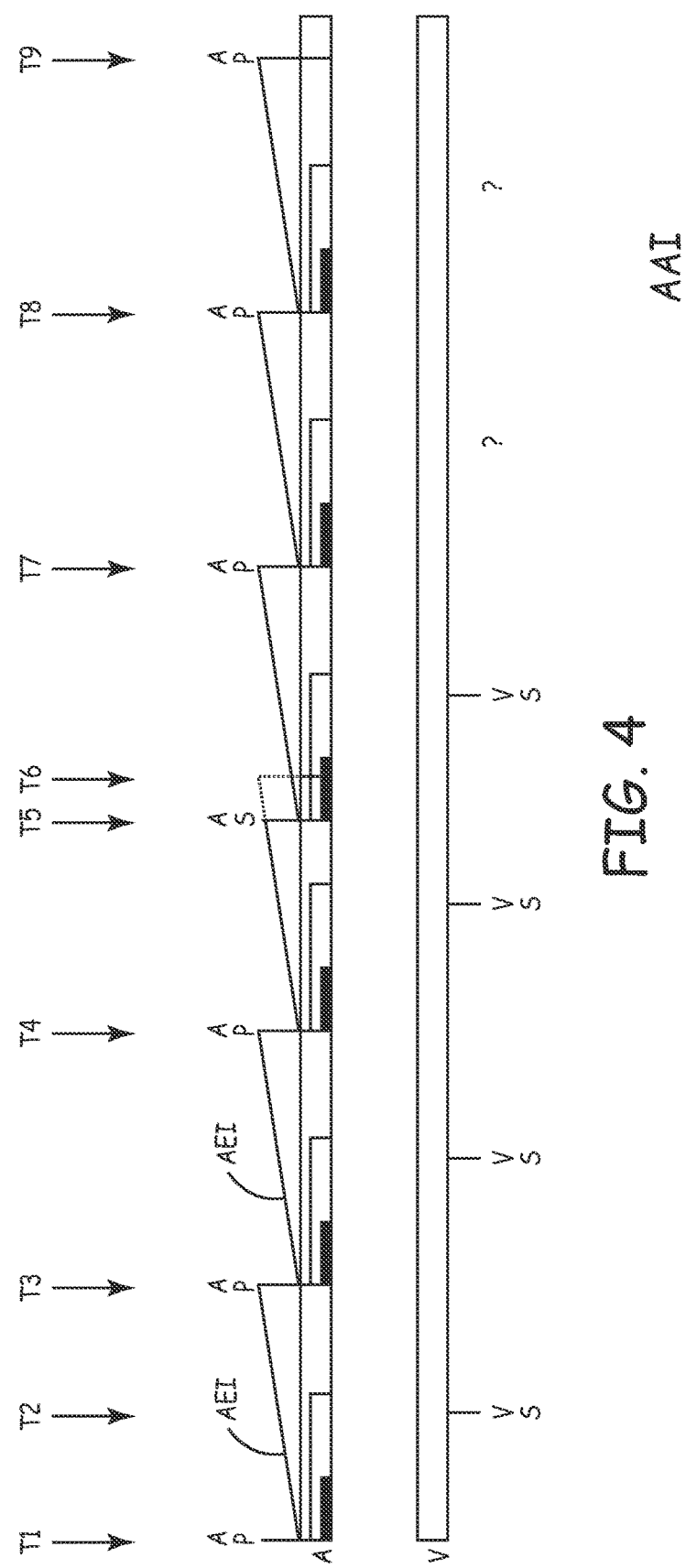
FIG. 4 is a ladder diagram illustrating the operation of an implantable medical device in an AAI mode of operation.

FIG. 4 is a ladder diagram illustrating how a device, such as ICD 10, will operate in an AAI mode and is also relevant to an understanding of the AAI/R, ADI, and ADI/R modes. It should be appreciated that a single lead device operating in AAI will be more limited than a device having multiple leads that is simply operating in the AAI mode. Thus, in a single lead device, the illustrated ventricular data would not be available, whereas in a dual chamber device the ventricular data is obtainable but is selectively ignored if operating in AAI.

Certain events are presented for illustrative purposes, however the following discussion of various modes is not meant to be exhaustive, limiting, or all-inclusive. As such, various elements are selectively omitted for clarity and various optional elements are presented for illustration. In addition, these modes may be implemented in variety of ways, thus the specific parameters presented should not be taken as limiting. For example, one device may define a cardiac cycle by an A-A interval whereas another may define it as a V-V interval. In addition, the modes are generally presented in their basic form with understanding that rate responsiveness, if provided, will modify the modes in a known manner.

The ladder diagram indicates certain events, intervals, and timers for an atrial channel A (upper bar) and a ventricular channel V (lower bar) over time. Atrial and ventricular events, paced or sensed, are indicated by vertical lines and the various timer or intervals are represented by slanted lines.

In the AAI mode, the device senses in the atrium, paces in the atrium, and inhibits pacing in the atrium if a proper event is sensed. For example, at time T1, an atrial pace AP is delivered. At the same time an atrial refractory period ARP and atrial blanking period ABP are initiated. These periods simply run for a predetermined length of time. During blanking, events are not sensed while during a refractory period events are sensed, but these sensed events are not used to restart certain timing intervals. This prevents, for example, atrial sensing and/or triggering based on far field R-waves. Also at T1, an atrial escape interval AEI or A-A escape interval is started. The AEI is simply a timed interval that is often programmable. At the end of the interval, an atrial pace (AP) is delivered, unless inhibited.

At time T2, an intrinsic ventricular event VS occurs as a result of normal conduction, triggered by the AP. At time T3, the AEI expires and an AP is delivered, restarting the process. This cycle may continue indefinitely.

At time T4, an AP is delivered that starts another AEI. Before the expiration of the AEI, an intrinsic atrial event AS occurs outside the ARP and is sensed. The AAI mode inhibits an atrial pace when an intrinsic atrial event is sensed. Thus, at time T6, when the AEI would have expired no AP is delivered. The next AEI is initiated by the AS at time T5. Thus, if there is intrinsic atrial depolarization occurring at a faster rate than the programmed lower rate interval LRI (corresponds to the illustrated AEI), then atrial pacing is inhibited. Rate responsiveness will alter these parameters in the known manner.

After the completion of the previous AEI, an AP is delivered at time T7 and the intervals are restarted. As indicated, there is no ventricular event during this or the subsequent cardiac cycle. Since the device continues to operate in AAI, the lack of a ventricular event has no effect. Atrial pacing is delivered normally at times T8 and T9.

Figure 5A:
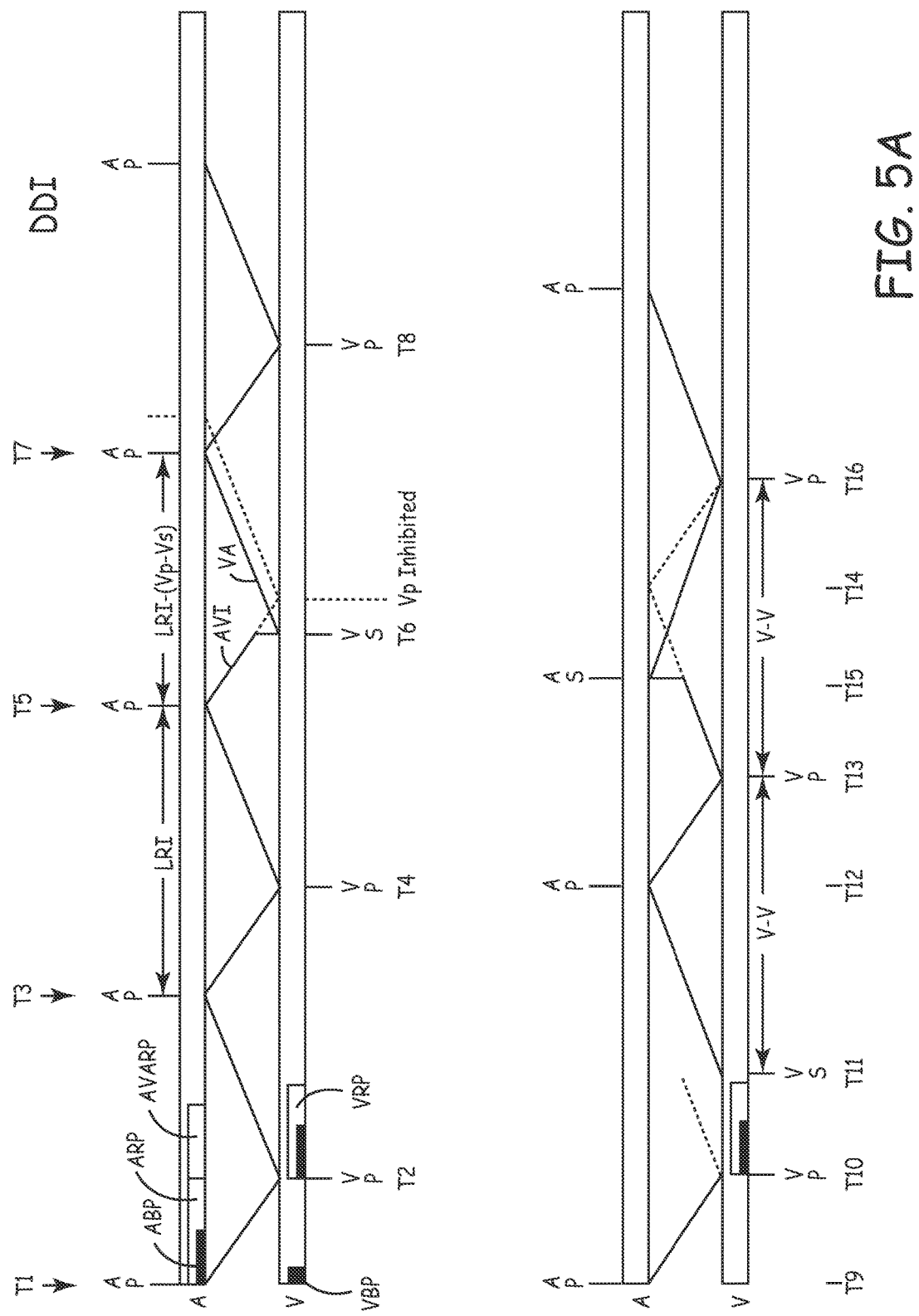
FIGS. 5A-5B are ladder diagrams illustrating the operation of an implantable medical device in a DDI mode of operation.

FIG. 5A is a ladder diagram illustrating operation in a DDI mode. In a DDI mode, there is sensing and pacing in both the atrium and ventricle, with pacing being inhibited if an appropriate intrinsic event is sensed. In the illustrated example, an atrial pace AP is delivered at time T1. Various blanking and refractory periods are initiated such as the ventricular blanking period VBP, the ARP, the ABP, the post-ventricular atrial refractory period PVARP, and the ventricular refractory period VRP, which includes a blanking period. The ARP and the PVARP together define the total atrial refractory period TARP.

An atrial-ventricular interval AVI (or AV interval) is also initiated at time T1. At the completion of the AVI, a ventricular pace will be delivered, unless inhibited by an intrinsic event. Thus, at time T2, the AVI expires and a ventricular pacing pulse VP is delivered. At that point, a ventricular-atrial (VA) interval is initiated. When the VA interval expires, an AP will be delivered unless inhibited and at time T3, the AP is delivered. The process repeats and a VP is delivered at time T4 and an AP is delivered at time T5. The time between the delivered APs at times T3 and T5 is equivalent to the lower rate interval LRI. That is, in the absence of intrinsic events (or rate responsiveness), the LRI is the lowest resultant cardiac rate allowed by the device.

At time T5, the AP is delivered and the AVI is initiated. Prior to completion of the AVI, an intrinsic ventricular event VS is sensed at time T6. The VS terminates the AVI and begins a VA interval of normal duration. The scheduled but inhibited VP is illustrated along with the timing of the VA interval that would have started with that VP. Thus, at time T7, the VA interval expires and the AP is delivered. The A-A interval defined between times T5 and T7 is shorter than the LRI by an amount of time equal to the time between the VS and the inhibited VP. With the AP at time T7, a new AVI is started and at time T8 the next VP is delivered. In this manner, paced V-V intervals remain constant.

For a fixed rate, the AVI and VA intervals are known. Thus, the device is configured to react ahead of time, or prior to the initiation point for a given interval.

Figure 5B:
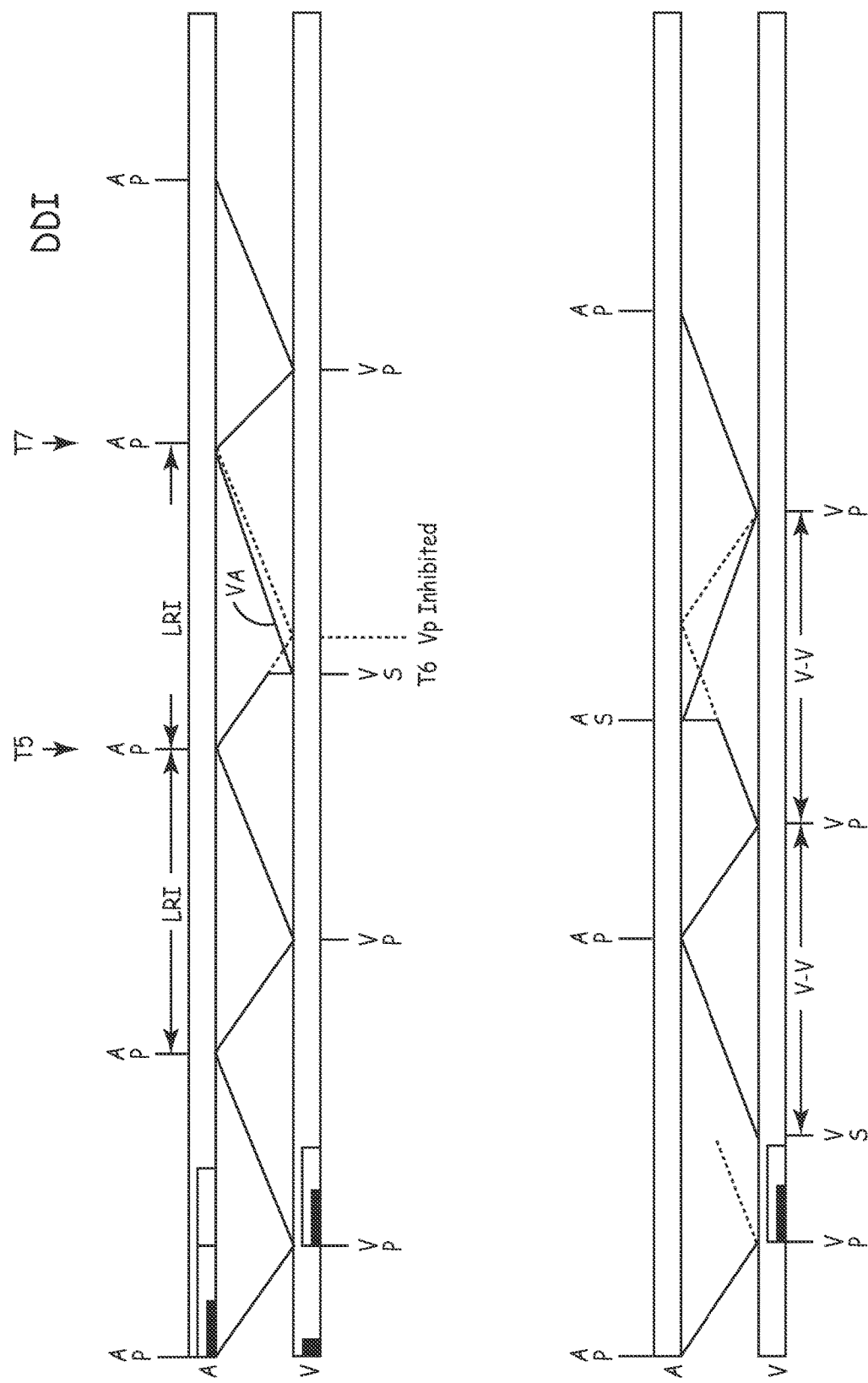

FIG. 5B illustrates timing similar to that of FIG. 5A except that A-A interval consistency is maintained when a ventricular sense occurs at time T6. In this embodiment, the VA interval that is initiated at time T6 is calculated and set to a longer time interval than compared to a "normal" VA interval (indicated by dashed lines). Thus, this longer VA interval expires at time T7 and thus the A-A interval corresponds to the LRI. As such, there is consistency between A-A intervals. Thus, the VA interval will be calculated and will be determined by the timing of the ventricular sense VS.

Continuing with FIG. 5A, an AP is delivered at time T9 and the AVI is initiated. A VP is delivered at time T10 and the next VA interval begins (hashed line); however, during the VA interval and after the VRP an intrinsic ventricular event VS (e.g., a premature ventricular contraction PVC) is sensed at time T11. The VS effectively restarts the full VA interval. If the restarted VA interval is allowed to complete, as illustrated, the next scheduled AP is delivered at time T12, with a VP following at time T13. Again, paced V-V intervals and VS-VP intervals remain constant.

With the VP at time T13, a VA interval is started. Prior to completion of the VA interval, an atrial event AS is sensed at time T14. The AP scheduled for time T15 is thus inhibited. A modified AV interval is "initiated" at the AS. The modified AV interval is longer than the normal AV interval so that the VP delivered at time T16 facilitates constant V-V timing. In other words, an AS does not really terminate the ongoing VA interval. Rather, that interval does continue to run and complete at time T15, the AP is inhibited, and the normal AV interval is started. Therefore, despite having to react to an AS and effectively elongate the AV interval, the timed intervals remain known, constant values that can instantly be implemented at the appropriate event, such as the expiration of the full VA interval at time T15.

Figure 6:
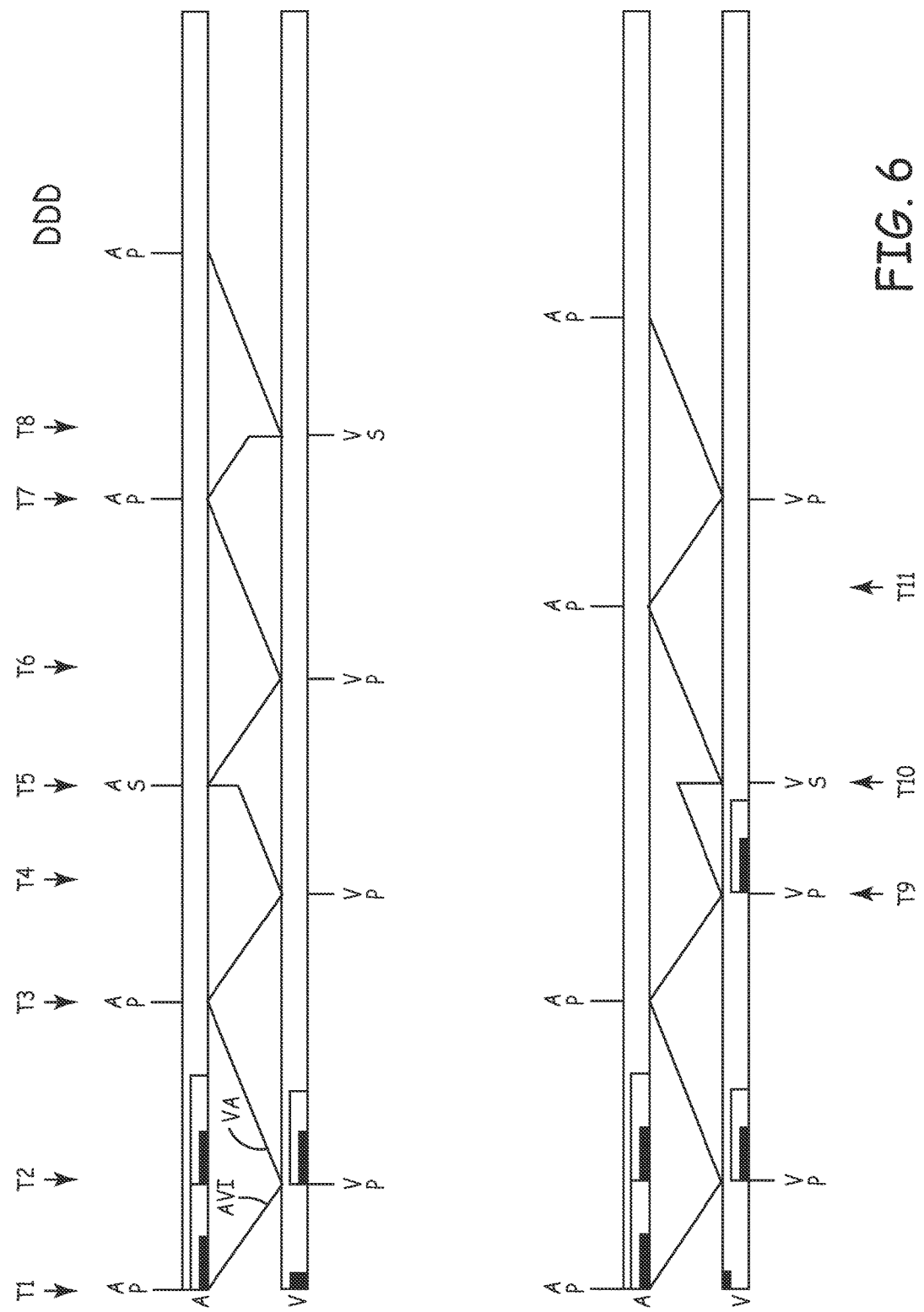
FIG. 6 is a ladder diagram illustrating the operation of an implantable medical device in a DDD mode of operation.

FIG. 6 is a ladder diagram that illustrates operation in a DDD mode. Thus, sensing and pacing occur in both the atrium and ventricles and the response can be inhibition or triggering. At time T1, an AP is delivered. The above described refractory and blanking periods are initiated. In addition, an AVI is started. At the completion of the AVI (time T2) a VP is delivered and a VA interval is started. The VA interval terminates at time T3 and an AP is delivered. The next VP is delivered at time T4 and the VA interval is initiated. Prior to the termination of that VA interval, an atrial event AS is sensed at time T5. This truncates the VA interval, inhibits the AP, and a new AV interval is started at time T5.

In the DDD mode, the various intervals are predetermined as previously described. However, there can be different intervals that are implemented depending upon whether the triggering event was paced or sensed. Thus, at T5 the AV (sensed) interval is initiated, which may be programmed to be the same as or different than the AV (paced) interval started at time T3. In any event, whether a sensed or paced event acts as the trigger, the subsequent interval that will start is predetermined.

Following the VP at time T6, the VA interval is initiated and upon completion, the AP is delivered at T7. A new AVI is started, but prior to completion a VS occurs at time T8. The VS terminates the AVI and initiates a VA interval. In some devices, the VA interval is selected at time T8 so as to maintain consistency in the A-A timing, which is referred to as atrial based timing. In other devices, the VA interval is predetermined but there may be a first predetermined VA interval following a paced event and a second predetermined VA interval following a sensed event, wherein the first and second interval can be programmed to the same or different values.

Following normal operation, a VP is delivered at time T9 and a VA interval is started. Prior to completion of the VA interval, a VS (PVC) occurs at time T10, which is outside of the refractory period. This restarts the VA interval, and upon completion, an AP is delivered at time T11.

A device such as ICD 10 may operate in any mode, such as AAI, DDI, DDD, or any number of other known modes. In addition, while operating in one mode the device may determine that another mode should be employed and effect a mode switch into that mode.

As described in the exemplary dual chamber modes discussed herein, a ventricular pacing pulse will be delivered following the expiration of an AVI. This is desirable in that AV synchrony is maintained; however, because of the practical considerations of the AVI, ventricular pacing pulses are often delivered even though intrinsic conduction would have eventually occurred, if sufficient time were allowed. Furthermore, as discussed in some detail in the applications incorporated by reference herein, there is increasing recognition that unnecessary ventricular pacing may have some undesirable consequences.

To eliminate all ventricular pacing, a mode such as AAI may be selected. As described, if intrinsic conduction fails in this mode, then there is no ventricular pacing provided and of course, this is more undesirable and harmful than extra ventricular pacing. As such, practitioners tend to err on the side of caution and rely on modes such as DDD.

The above referenced related applications include a number of protocols for reducing, limiting, optimizing and/or minimizing ventricular pacing. As used herein, terminology such as "managed ventricular pacing," "managing ventricular pacing," or "ventricular pacing management" (and grammatical variations thereof) is meant to refer to these protocols individually or collectively. As these protocols relate to the present invention, a general overview is presented; however, this discussion is merely illustrative of the concepts, is not meant to be exhaustive, and is in no way intended to limit these inventive concepts.

Figure 7:
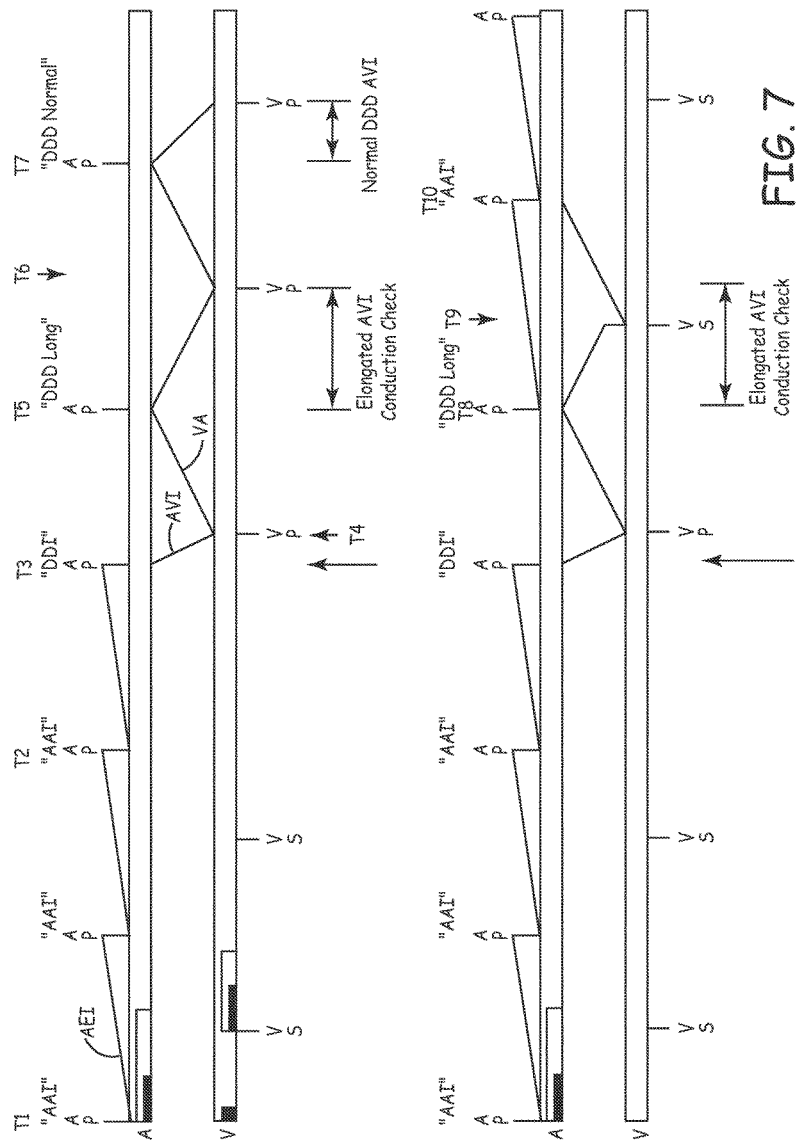
FIG. 7 is a ladder diagram illustrating the operation of an implantable medical device while managing ventricular pacing according to one embodiment of the present invention.

In a first embodiment illustrated in FIG. 7, ventricular pacing is managed through a mode switching protocol that uses an "AAI" or "ADI" mode (again these designations are used as approximations of the programmed behavior). Generally, under this protocol, intrinsic conduction is given a maximum opportunity to present itself in a given cardiac cycle and to facilitate that opportunity, a full cycle may pass without ventricular activity. In other words, this protocol will tolerate one skipped ventricular beat in order to maximize the potential for intrinsic conduction.

To begin with, the protocol operates in this "AAI" mode and at time T1, an AP is delivered. Unlike true, single lead AAI, the ventricular events are sensed and as long as a ventricular event is sensed anywhere within a given A-A interval, the protocol remains in this "AAI" mode. Two normal cycles are illustrated and at time T2, an AP is delivered. At the same time, the atrial escape interval AEI is started and expires at time T3. At T3, the next scheduled AP is delivered normally; however, no VS occurred between T2 and T3. If a VS had occurred at any time prior to T3, then the device would have remained in this "AAI" mode. Since no VS occurred, the device mode switches to DDI at time T3 and after a shortened (with respect to typical DDI operation) AVI, delivers a support pace at time T4. Thus, one A-A cycle has progressed without ventricular activity; however, on the next cycle the mode switch to DDI assures ventricular depolarization.

Consistent with one embodiment of managed ventricular pacing, the device mode switches to a "long" DDD at time T5. In actuality, under this embodiment, the device will "know" that after one cycle of DDI, a switch will occur to DDD. That switch or preparation for the switch can therefore occur or begin to occur at any point between times T4 and T5. In any event, the AVI initiated at time T5 is longer relative to normal DDD pacing. As such, there is a greater opportunity for intrinsic ventricular depolarization. If intrinsic activity is sensed, then the device mode switches back to "AAI". As illustrated, the AVI expires without an intrinsic sense, thus the VP is delivered at time T6. The next VA interval is started and expires at time T7 and an AP is delivered. At the same time, the device now operates in a normal DDD mode. This is not a mode switch; rather, the value for the AVI is set to the normal duration. The device will continue to operate in DDD for some time and then periodically check for intrinsic conduction. If able, the device will switch to "AAI" if such intrinsic conduction is found.

In FIG. 7, time T8 indicates the delivery of the AP in DDD "long" as described above (the cycles immediately proceeding time T8 correspond to those previously described and prior to time T5). The elongated AVI is initiated and prior to its expiration, a VS occurs at time T9. The VS terminates the AVI and a VA interval is started. At the completion of the VA interval (time T10), the AP is delivered and the device mode switches to "AAI." Once the VS occurs, the device can prepare for the mode switch that will affect the next cycle. This sequence demonstrates the preference for allowing intrinsic conduction and the ability to switch back to "AAI" when intrinsic conduction is present.

Figure 8:
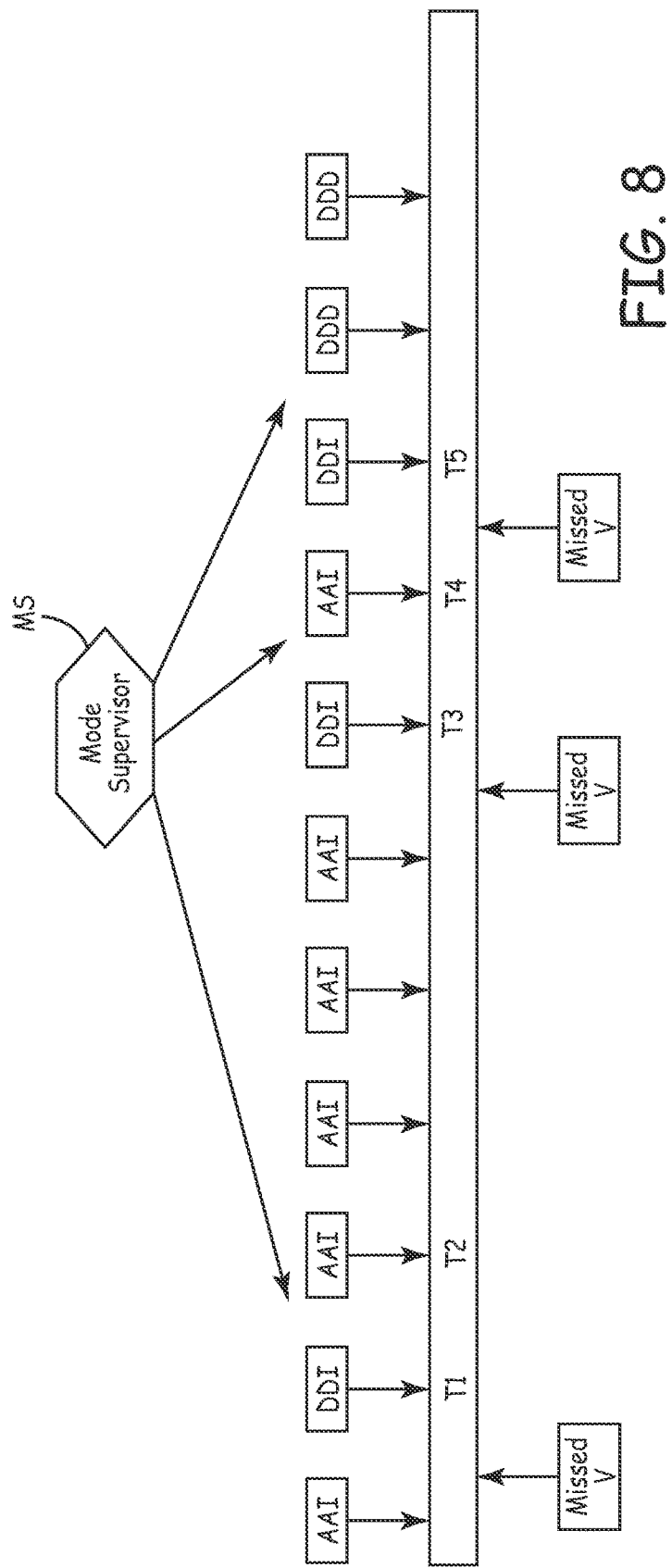
FIG. 8 is a ladder diagram illustrating the operation of an implantable medical device with a mode supervisor.

FIG. 8 illustrates another embodiment of ventricular pacing management. A mode supervisor MS monitors the events that are occurring and imposes a set of rules for, among other things, mode switching. The mode supervisor MS is a program, protocol, or module that resides in hardware, software, or firmware and is distinct from the modes themselves. The mode supervisor will utilize data to institute mode changes and other operations based on data that goes beyond what governs a given mode. A mode is defined by a series of logical operations. The mode supervisor gathers additional information such as e.g., trends, history or patterns, and makes decisions that are not limited to the current set of mode specific logical operations.

For example, in one embodiment, the device will mode switch to DDI (time T1) after a complete A-A cycle without ventricular activity in the same manner as previously described. However, the base protocol will then always mode switch back to "AAI" (time T2) for the very next cycle (as opposed to switching to DDD, etc.). Thus, the base mode will allow one cycle to complete without ventricular activity, but not two sequential cycles. If intrinsic conduction were completely blocked, then the base mode would switch back and forth between "AAI" and DDI. This would effectively halve the ventricular rate and would be undesirable over a period of time. Thus, the mode supervisor MS monitors the activity and alters the mode when certain conditions are met.

For example, in one embodiment the mode switch back to "AAI" from DDI is only permitted if there was ventricular activity in three of the last four A-A intervals. Thus, at time T3, a mode switch to DDI occurs and the mode supervisor MS determines that of the previous four cycles, at least three had ventricular activity. Here, the base mode is allowed to mode switch to "AAI" at time T4.

The device again mode switches to DDI at time T5 due to the absences of ventricular activity in the preceding A-A interval. This time, the mode supervisor MS notes that there were less than three of the last four cycles with ventricular activity. Thus, the mode supervisor MS causes the device to mode switch from DDI to DDD, rather than back to "AAI." The mode supervisor may periodically thereafter recheck for intrinsic conduction and if found, switch back to "AAI." The mode supervisor may act under a variety of parameters and rule sets to guide the mode switching. Various patterns or parameters are provided that will cause the mode supervisor MS to initiate a particular action.

In summary, the device operates in "AAI" until a complete A-A interval transpires without ventricular activity. This presents a maximum amount of time to allow for intrinsic conduction for a given cycle, i.e., the whole cycle. After an A-A interval without ventricular activity, the device mode switches and delivers a ventricular pacing pulse. Thus, atrial tracking occurs and there are not an undue number of sequential A-A intervals without ventricular activity. As described, there are a number of embodiments presented that address the activities following the mode switch from "AAI" to the dual chamber mode (DDI or otherwise) where ventricular pacing is delivered.

The protocols for managing ventricular pacing can be implemented in devices as they have been previously described. Depending upon the practical limitations of the particular hardware, software and operating parameters of a given device, the timing of the mode switching may present certain difficulties. In addition, the same difficulties may be present in some cases if the ventricular management protocol is programmed into existing devices.

Referring again to FIG. 7, the device is operating in "AAI" until time T3. At time T3, the previous AEI is expiring, the AP is delivered and the device is mode switching to DDI. In other words, the device must simultaneously determine that a mode switch is required and implement that mode switch. That is because a VS could occur at any point during the AEI. It is only really at or after the expiration of the AEI that the device can determine that no VS occurred and react accordingly.

Again, at the same point in time T3, the AVI (in DDI) is started. This is a timer that starts when a triggering event occurs (e.g., AP, expiration of AEI). Thus, that timer must be set and readied to start prior to that triggering event occurring; otherwise a delay is imposed in readying and initiating the timer. The mode switch itself takes some finite amount of time and the rules, operating parameters, and values for the various intervals and timers must be obtained and then started. As a practical matter certain hardware/software configurations may not be able to perform all of these functions simultaneously especially in the limited environment of implantable medical devices, thus resulting in an added delay. Depending on the duration, the resultant delay could be problematic.

The subsequent mode switches (e.g., DDI to DDD) are not necessarily problematic as their occurrence is known or anticipated in the cycle before their implementation. Thus, the device has sufficient time to initiate and make the mode switch. In other words, the device "knows" that at some future point in time or when some future sensed event occurs, a mode switch will occur, thus the values required can be obtained and readied.

For those devices that would otherwise have an unacceptable or undesirable delay in implementing the protocols, one embodiment of the present invention provides for a mode switching protocol that achieves the same results as illustrated in FIGS. 7 and 8, while obviating the above noted delay issues. This embodiment is referred to herein as "AAI biased DDI".

Figure 9:
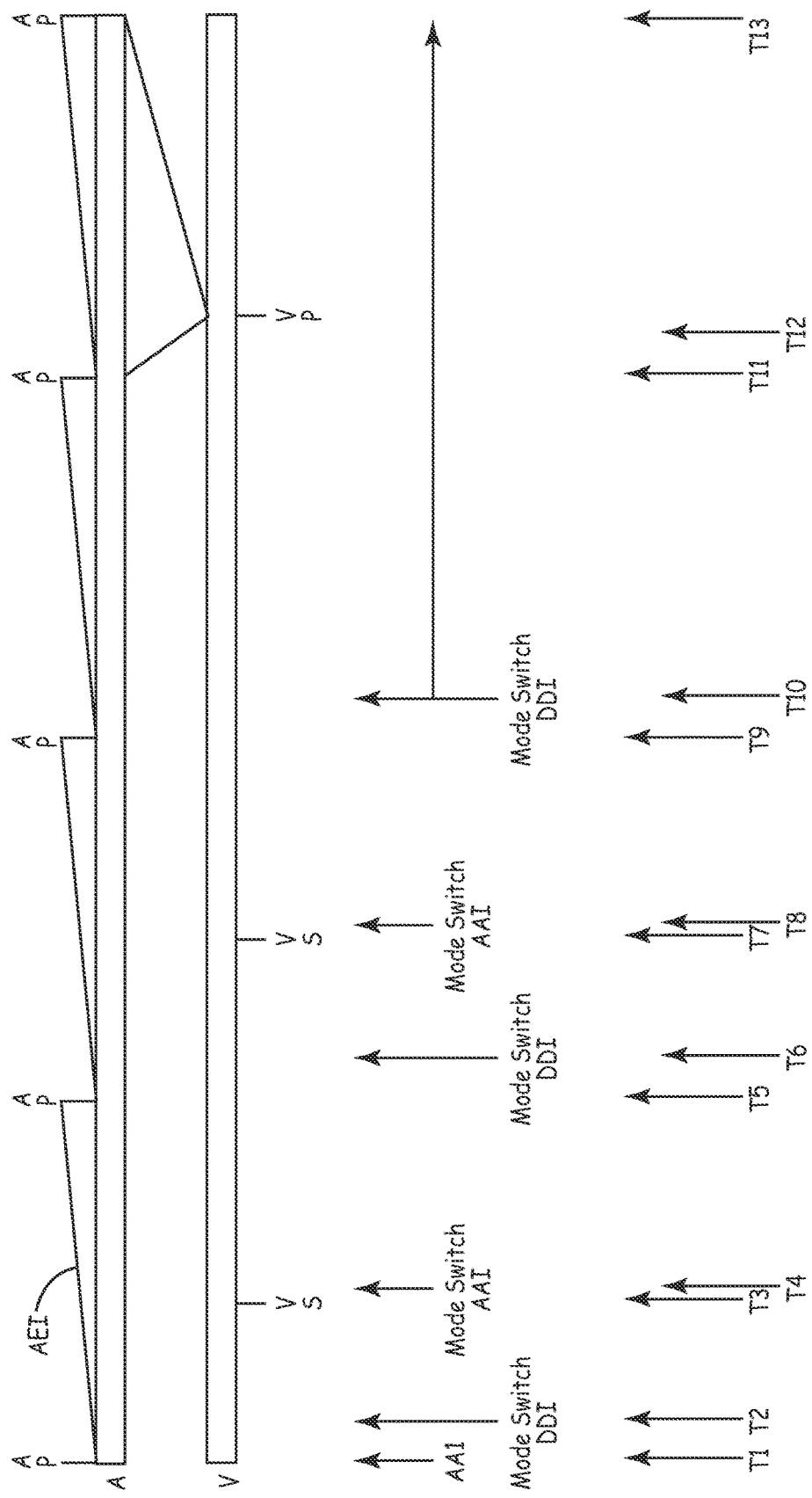
FIG. 9 is a ladder diagram illustrating the operation of an implantable medical device while managing ventricular pacing according to another embodiment of the present invention.

With reference to FIG. 9, normal ventricular conduction has occurred prior to time T1. Thus, at time T1, the device delivers an AP while operating in AAI mode. With the delivery of the AP an AEI is initiated. By definition within the AAI mode protocol, an AP will be delivered when the AEI expires unless inhibited by an intrinsic atrial sense. Subsequent to the initiation of the AEI, the device mode switches to DDI at time T2. Though the device is now in the DDI mode, the behavior generally does not change for the current A-A interval. In other words, the mode switch to DDI occurs but does not stop or interrupt the AEI, which continues to run and upon expiration the scheduled event will happen, regardless of the switch to DDI.

Intrinsic conduction occurs and at time T3, a ventricular event is sensed. Because the ventricular event is sensed, the device mode switches back to AAI immediately or shortly thereafter at time T4. Neither of these mode switches has affected the AEI which expires at time T5 and an AP is delivered. Since the device has been in AAI since time T4, the mode dictates the initiation of a subsequent AEI at time T5.

This process is repeated over the next A-A cycle with time T5 to T9. Again, at time T9 an AP is delivered while in AAI and an AEI is initiated. At time T10 the device mode switches to DDI and the AEI continues to run. As illustrated, there is no VS and thus, nothing to trigger the mode switch back to AAI; hence the device remains in DDI when the AEI expires at time T11. The expected action at the expiration of the AEI is the delivery of an AP, which occurs at time T11. Since the device was in DDI at this time, a AV interval begins at time T11 and expires at time T12 with the delivery of a VP. At the same time, a VA interval is started and expires at time T13. If a subsequent mode switch is to happen, it may take place at any point after time T12.

Returning to the time period between T10 and T11, the device operates in DDI even though the AEI is running. Thus, unless cancelled by a subsequent mode switch, the device "anticipates" initiating an AV interval at the expiration of the AEI and makes ready to do so. Therefore, there is no delay at time T11 that might otherwise occur if the device had mode switched from AAI to DDI at this point in time. Similarly, if a VS does occur, the mode switch from DDI to AAI occurs with sufficient time for the device to make ready to initiate a subsequent AEI.

Figure 10:
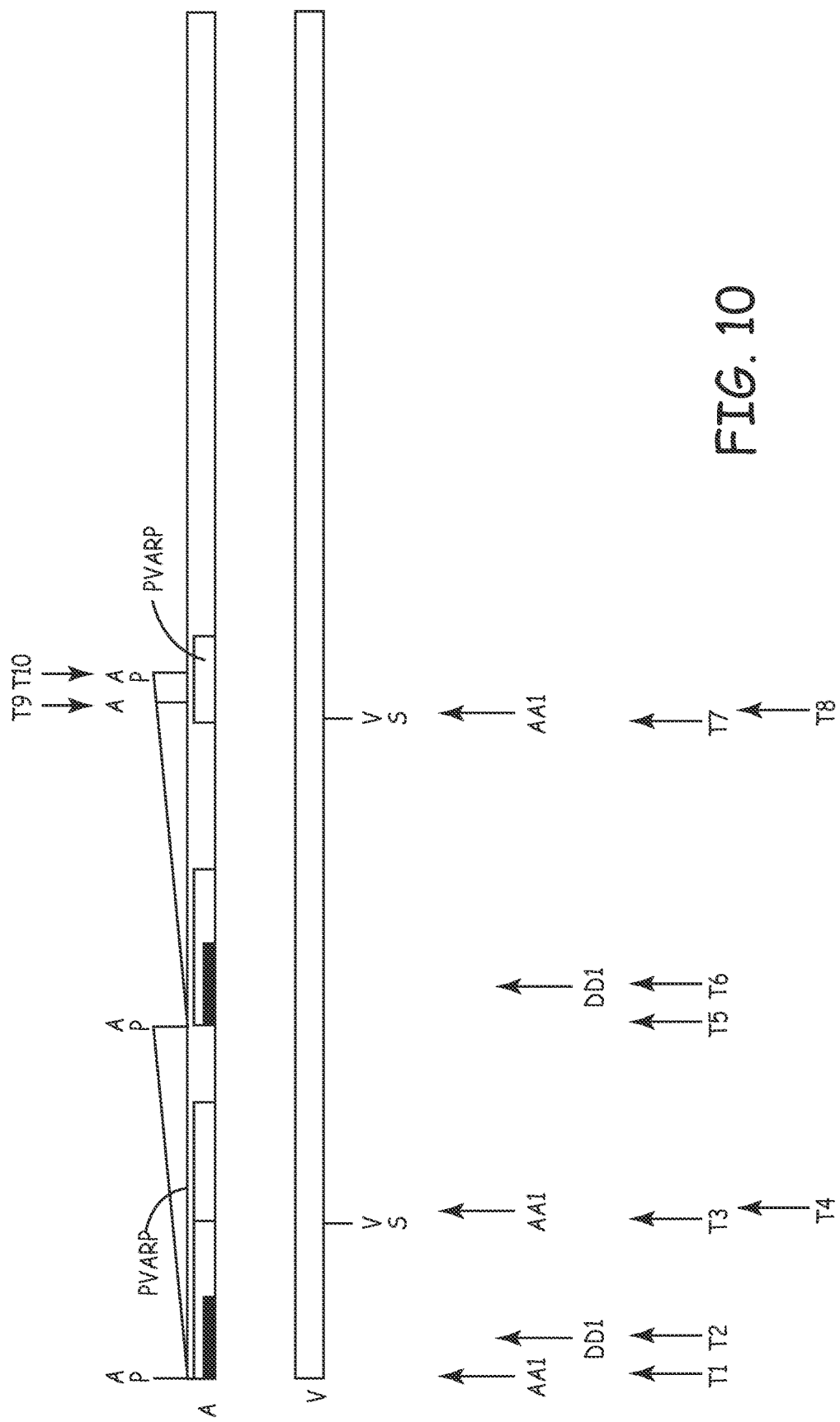
FIG. 10 is a ladder diagram further illustrating the operation of an implantable medical device.

While the above embodiment eliminates the previously discussed delay issues, certain anomalies could occur in some special circumstances. FIG. 10 illustrates the operation of the device in AAI biased DDI. The sequence begins with an AP at time T1. At this point, the device is in AAI and an AEI is initiated. The atrial refractory period ARP and atrial blanking period ABP also begin. Subsequently, the device mode switches to DDI at time T2. At time T3, a VS occurs. The VS triggers a mode switch back to AAI at time T4. As the device was operating in DDI when the VS occurred, a PVARP (post-ventricular atrial refractory period) is initiated and runs very briefly. This occurs because the mode switch to AAI is not instantaneous and furthermore, the termination of the PVARP takes some small period of time to process. While this overlap of time does not critically affect the overall timing or performance of the operations, it produces an anomaly in that the PVARP does actually begin and run for a brief period of time before the mode switch to AAI is achieved.

After switching to AAI at time T4, the AEI expires and the next AP is delivered at time T5. The next AEI is initiated and the device subsequently mode switches to DDI at time T6. At time T7, a late VS does occur. As the device is in DDI, a PVARP begins. At time T8, the device mode switches to AAI. As previously indicated, there is a brief delay before the PVARP can be cleared. During that time, an intrinsic atrial event A occurs but is blanked and thus not recognized by the device. Subsequently, the AEI expires and the scheduled AP is delivered at time T10. It should be appreciated that the exact timing of the switch to AAI and the intrinsic atrial event relative to one another or their temporal sequence is not important; the issue is the amount of time that the PVARP runs before clearing and whether an atrial event occurs during that time.

Such a scenario is rare and may have no effect as the atria may already be refractory; however, such extraneous pacing is undesirable and is preferably avoided. With multiple mode switching, other such anomalies are possible. To avoid them, one solution is to modify or eliminate the various refractory/blanking periods that are potentially at issue. Of course, this requires additional programming and complexity and also eliminates the benefits of such features. The use of AAI biased DDI may be desirable in cases where existing devices or infrastructure are reprogrammed or modified, but need to rely on existing and available parameters. Whether or not such anomalies occur and whether or not such anomalies, if present, would lead to problematic conclusions will determine if and how AAI biased DDI will be incorporated into a given device.

In the above described embodiments, the protocols used to manage ventricular pacing rely on the ability to switch between various modes according to the rules established by the controlling protocol. The present invention also provides for a new pacing mode that is referred to as "fully inhibited DDI" (FIDDI) or a "fully inhibited dual chamber" (FIDC) mode. Once again, reference to DDI in this context is a matter of convenient nomenclature that does not in any way limit the present invention. FIDDI and DDI are completely distinct and separate modalities and should not be confused. As will become apparent, the FIDDI mode has certain characteristics that facilitate the management of ventricular pacing; however, FIDDI is not limited to such a purpose and may be readily applied in a variety of situations, as it is a new and independent pacing modality.

Figure 11:
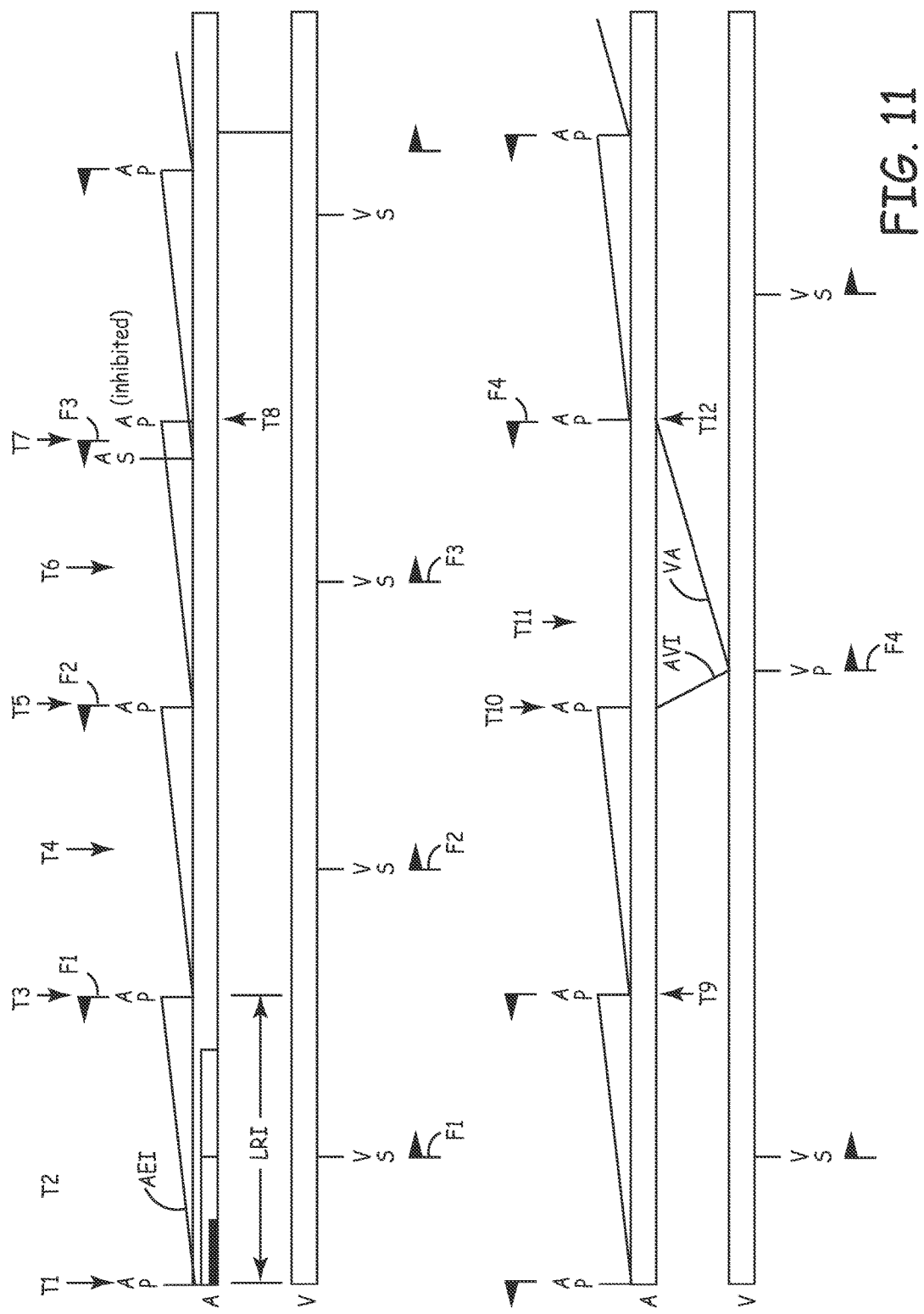
FIG. 11 is a ladder diagrams illustrating the operation of an implantable medical device in a fully inhibited DDI (FIDDI) mode of operation, according to one embodiment of the present invention.

Operation of a device in one embodiment of FIDDI is illustrated in FIG. 11. An atrial pacing pulse AP is delivered at time T1. An atrial escape interval AEI or A-A interval is started at the same time. The AEI defines the lower rate interval LRI and rate responsiveness, if utilized, will affect the FIDDI parameters in the known manner. At the expiration of the AEI, an atrial pulse will be delivered. If an atrial event is sensed prior to the expiration of the AEI, then the AP is inhibited and the next AEI is initiated. The various blanking and refractory periods can be employed on both the atrial and ventricular channels if desired, and will not be described in detail.

During the AEI initiated at time T1, an intrinsic ventricular event VS is sensed at time T2. The ventricular sense causes flag F1 to be set in memory. The AEI continues until it expires at time T3. The device reads the appropriate memory location and identifies the presence of flag F1. Because flag F1 is present, the next AP is delivered at time T3 and another AEI is initiated. A flag will be set for the next cardiac cycle if a VS occurs at any time during a given AEI.

As used herein, a flag is simply an indicator that can be selectively set and its presence or absence may be identified at a later time by the device or a component thereof. For example, the flag may be any analog or digital data or indicator placed into any form of memory, a physical component that is actuated, a switch that is opened or closed, a signal that is generated within circuitry, a voltage or current level, or any other discernable indicator. While the flag is described as being set in response to criteria (e.g., ventricular activity) the converse is equally applicable. That is, the flag may be preset and then removed if ventricular activity is present; thus, the absence of the flag rather than its presence indicates ventricular activity.

Subsequently, at time T4 a VS occurs and sets flag F2. At the expiration of the AEI, the next AP is delivered at time T5. Since the flag F2 was set, the AP is delivered and the next AEI is started. As illustrated, the device checks for the presence of the flag at the expiration of the AEI. Alternatively, when the flag is initially set at T4 or thereafter, the device can determine the proper course of action that will be taken at the expiration of the AEI. In other words, the device can wait until the end of the AEI and check for the flag or react to the set flag (or the ventricular activity itself) at an earlier time. Of course, the VS could occur close to the expiration of the AEI and will still have the same effect.

The AP is delivered at T5 and the next AEI is started, since there was a flag F2. Prior to the expiration of the AEI, there is an atrial sense AS at time T7. Thus, the AP that would have been delivered at time T8 is inhibited. In addition, the next AEI is initiated from the AS at time T7. The AEI is initiated because flag F3 was present, as it was set at time T6 due to the VS.

Assuming a normal progression of cycles, a flagged AP is delivered at time T9 and the next AEI is started. In this cycle, the AEI expires with no VS having occurred. Hence, no flag was set. At time T10, the AP is delivered. Without a flag being present, the next AEI is not started. Rather, an AV interval is initiated. The AV interval may be set to a relatively short interval, e.g., 80 ms so as to deliver a support pulse. Of course, the interval selected may be programmed as desired. Whatever time interval is programmed will be initiated at the AP, without the flag having been set. After the AV interval expires, the VP is delivered at time T11. Because there was a ventricular event, in this case a VP, flag F4 is set. A VA interval is commenced at time T11. At time T12, at the expiration of the VA interval an AP is delivered and since flag F4 was set, a subsequent AEI is initiated.

Figure 12A:
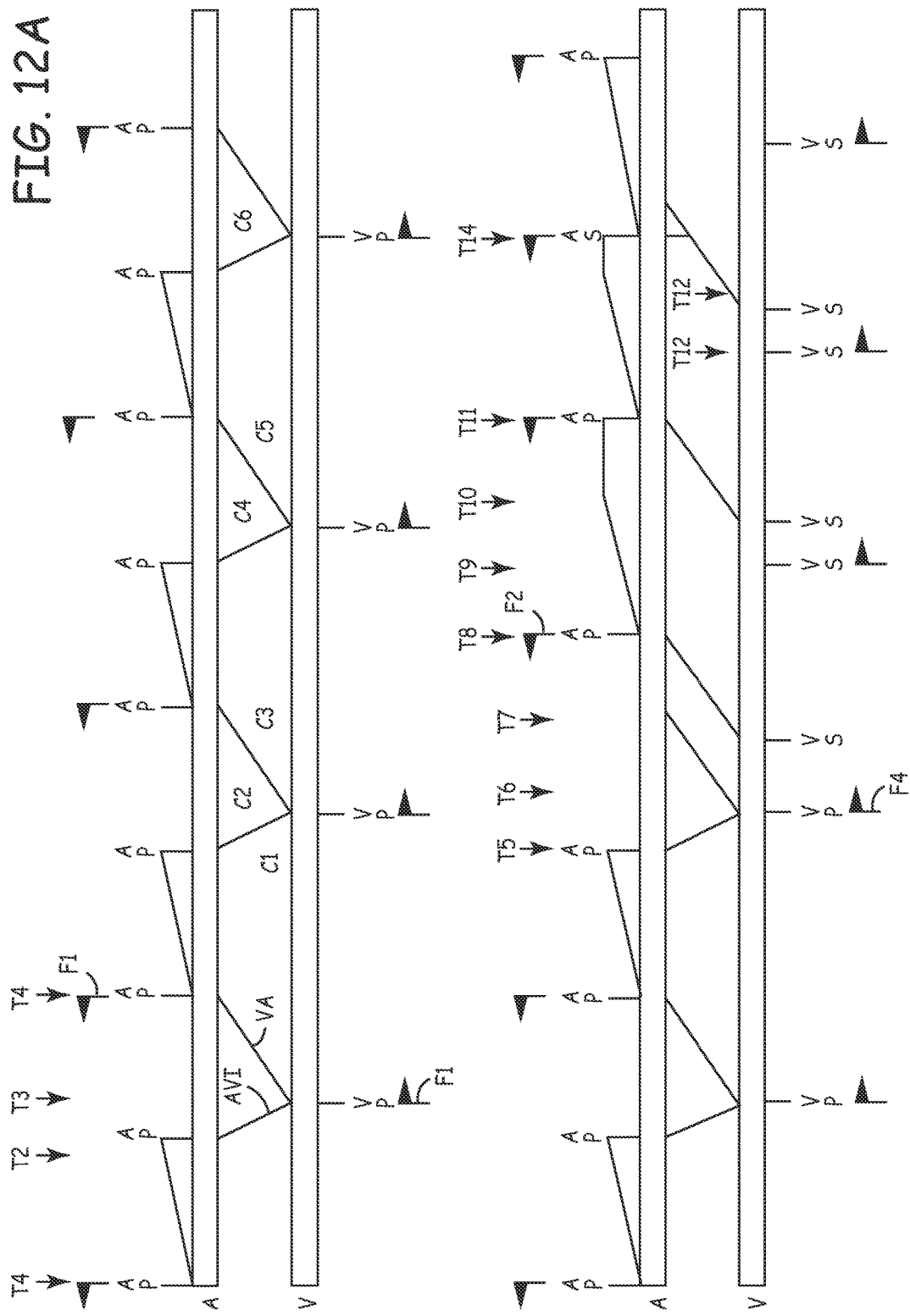
FIGS. 12A-12B are ladder diagrams illustrating the operation of an implantable medical device in a fully inhibited DDI (FIDDI) mode of operation, according to one embodiment of the present invention.

FIG. 12A is a ladder diagram also illustrating the operation of a device in the FIDDI mode. At time T1, the AP is delivered and the AEI is initiated. During the AEI, there was no ventricular sense and hence, no flag is set. At time T2, the next AP is delivered and the preprogrammed AV interval is initiated. At the completion of the AV interval, a VP is delivered at time T3 and a VA interval is initiated. The VP sets the flag F1. Subsequently, at time T4, the next AP is delivered and since flag F1 was set, an AEI is started. Without intrinsic ventricular events, the device alternates between cardiac cycles without ventricular activity and cardiac cycles with a paced ventricular event. In other words, there is ventricular activity every other cycle. Cycles C1, C3, and C5 are devoid of ventricular activity and cycles C2, C4, and C6 include ventricular support pacing. In its base mode, this is how FIDDI will act when a patient has, for example, complete conduction block. Leaving a patient in this pacing pattern for long periods of time would be undesirable, as this would effectively halve the ventricular rate. However, FIDDI in its base form is useful for facilitated atrial threshold pacing tests, as will be explained in greater detail below.

With continued reference to FIG. 12A, an AP is delivered at time T5, without a flag having been set. Thus, an AV interval is initiated and at its completion a VP is delivered at time T6. Thus, flag F2 is set and the VA interval is commenced. Prior to the completion of the VA interval, an intrinsic ventricular event is sensed at time T7. This VS, could be for example, a premature ventricular contraction (PVC). The VS will have no effect on the set flag. That is, flag F2 has been set and need not be modified. However, with the VS the VA interval is reset. This VA interval expires at time T8, the next AP is delivered and since flag F2 was set, the next AEI is initiated. Thus, in FIDDI each subsequent ventricular event sensed after a ventricular pace will reset the VA interval.

A flagged AP is delivered at time T8 and an AEI is initiated. Subsequently, there is intrinsic ventricular activity sensed at time T9 and a flag is set for the next cycle. Prior to the expiration of the AEI, another ventricular event is sensed at time T10. With a second (or subsequent) ventricular event occurring in a given A-A interval, the AEI is terminated and a VA interval is started at time T10. That is, the AEI is effectively extended. At the end of the VA interval, an AP is delivered at time T11. Had there been additional ventricular events during the VA interval, the VA interval would be reset with each event.

For the next cycle, an AP is delivered at time T11 and the AEI is started. A VS occurs at time T12 and before the expiration of the AEI, a second VS occurs at time T13. Just as in the previous cycle, this subsequent ventricular event triggers a VA interval that effectively elongates the AEI. Rather, the AEI is no longer applicable and the VA interval is the timer in use; as a practical matter the A-A interval is extended beyond what the AEI would have produced. Prior to the VA interval expiring, an AS occurs at time T14. Since the flag is set, this intrinsic atrial event initiates the start of the next AEI.

Figure 12B:
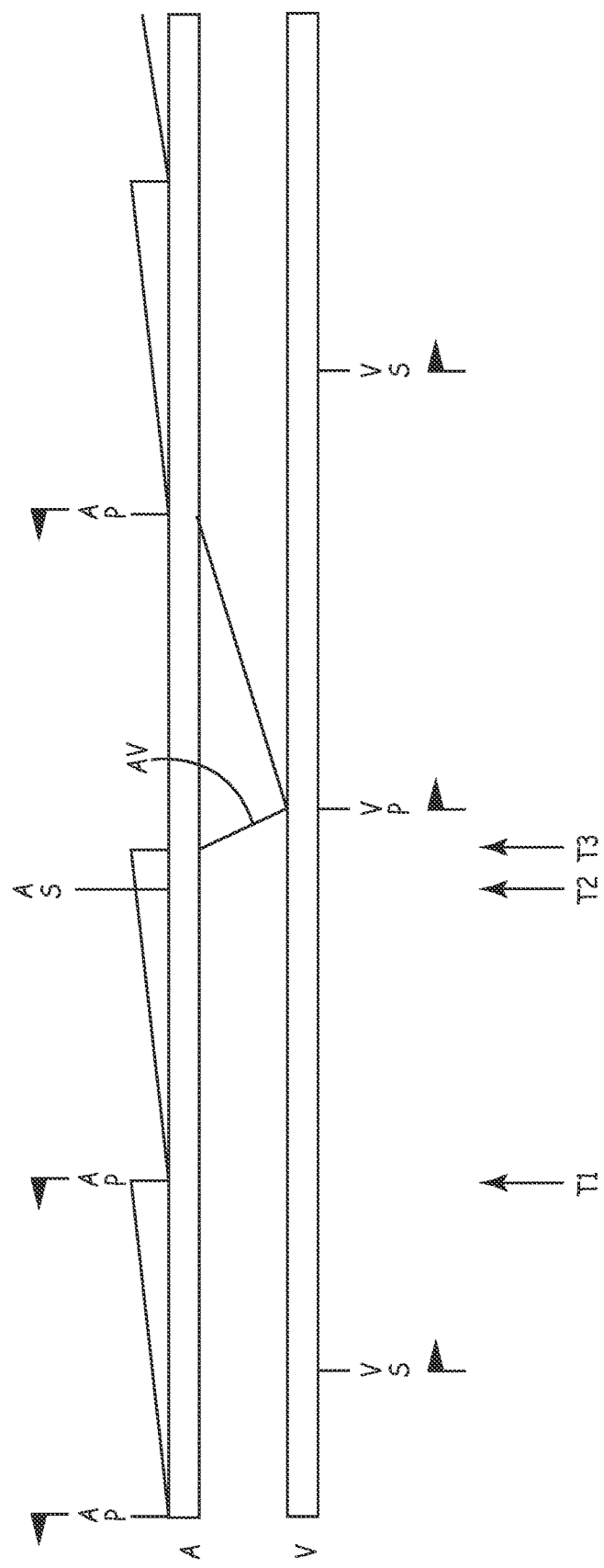

FIG. 12B illustrates an example where an intrinsic atrial sense occurs in a cycle where no flag has been set. At time T1, the AP is delivered and the AEI is initiated. No ventricular event is sensed and at time T2, an intrinsic atrial event is sensed. This will inhibit the delivery of the subsequent AP, which would have occurred at time T3. Even though the AP is inhibited, the AEI continues to run and upon its expiration at time T3, an AV interval is started. This will maintain consistency between A-A intervals. Alternatively, the AV interval could be initiated at time T2, if such consistency is not desired.

In general, FIDDI sets a flag in a given cardiac cycle that is valid for a subsequent consecutive cardiac cycle. As such, no more than one consecutive cardiac cycle will transpire without ventricular activity. For example, if there is complete conduction block FIDDI will pace every other cardiac cycle. It should be appreciated that various other embodiments of FIDDI are included within the scope of the present invention. For example, the parameters may be adjusted so that a given flag is valid for additional, subsequent cycles. If the flag is valid for, e.g., two cardiac cycles then two consecutive missed ventricular beats would be tolerated. In terms of complete dependence upon ventricular pacing, the device would then pace every third cycle. Therefore, by adjusting the number of cardiac cycles a flag is valid for, the number of consecutive missed ventricular beats permitted is correspondingly adjusted while maintaining atrial tracking.

As stated, in its base mode of operation FIDDI will, in one embodiment, tolerate a condition where only every other cardiac cycle (e.g., A-A interval) includes ventricular activity (e.g., complete conduction block). With lesser degrees of block or under other circumstances, other sequences will result but at least every other cycle will include a ventricular event. In the most extreme case, this results in a halved ventricular rate. A halved ventricular rate (with a normal atrial rate) will sustain life, but would lead to a poor quality of life. That is, such a ventricular rate over time would have negative consequences for the patient's health and well-being.

FIDDI is a complete pacing modality that will act according to the above described rules and parameters without mode switching. Therefore, if implemented in a device, FIDDI will achieve management of ventricular pacing in many situations. For example, in a patient where intrinsic conduction occurs in the vast majority of cardiac cycles, FIDDI will fully facilitate such conduction, tolerate a missed ventricular beat for a cycle, provide support pacing in the next cycle, and then continue to facilitate intrinsic conduction. In addition, in situations where atrial overdrive pacing is utilized, the rate halving effect of FIDDI may be desirable.

In other situations, FIDDI alone may result in undesirable long-term pacing patterns (e.g., ventricular rate halving with a normal atrial rate). Thus, the present invention includes various protocols for using FIDDI for ventricular pacing management.

Figure 13:
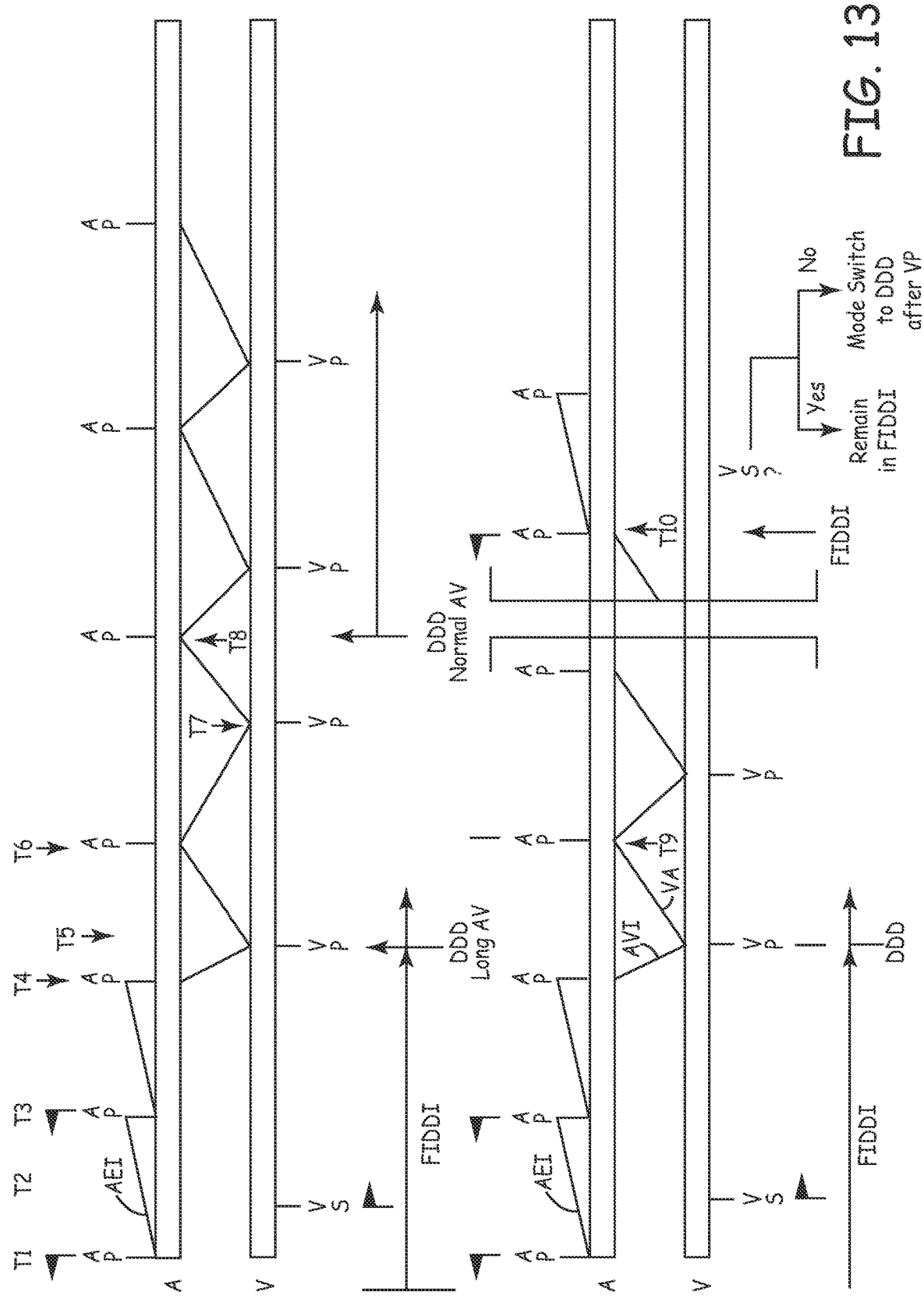
FIGS. 13-14 are ladder diagrams illustrating the operation of an implantable medical device in the FIDDI mode of operation while managing ventricular pacing.

Referring to FIG. 13, FIDDI is used in combination with mode switching to manage ventricular pacing. Prior to time T1 the device has been operating in the FIDDI mode. At time T1, an AP is delivered and because the flag was set, an AEI is started. A VS occurs at time T2 and sets a flag. Then, at time T3, the next AP is delivered and the next AEI is started. No ventricular sense occurs and at time T4 the AEI expires, an AP is delivered and an AV interval is started. At the end of this AV interval, a ventricular support pace is delivered at time T5 and a VA interval is started. Through this point, the device has operated in the FIDDI mode thus eliminating any delay issues.

During the AV interval, the device prepares for a mode switch from FIDDI to DDD. At the end of the AV interval, the next VP is delivered at time T5 and the device does in fact mode switch to DDD. As in previous embodiments, the first cycle of DDD is referred to as "DDD long" with an extended AV interval to allow for intrinsic conduction. This is optional, as the mode switch could be made to a normal DDD mode. In the illustrated example, the extended AV interval begins and expires at time T7 with the delivery of a ventricular pace. If there was a ventricular sense, the device could revert to FIDDI for the next and subsequent cycles. Without sensed ventricular activity, the device operates in "normal" DDD at time T8; that is, the AV interval is of a normal duration.

The device will continue in DDD mode until a conduction check is to occur. For example, at time T9 the device mode switches for FIDDI to DDD and operates in DDD mode for some period of time. After some predetermined interval, the device conducts a conduction check at time T10 wherein the device mode switches to FIDDI. Since the last cycle of DDD included a ventricular event (presumably paced), a flag is present at time T10 and an AP is delivered. The flag may actually be set or the default could be to assume that the flag is present for the first cycle after a mode switch to FIDDI. In either case, an AEI is started at T10 and the device monitors whether or not an intrinsic ventricular event occurs at any point during that AEI. If there is a VS, then the device will remain in FIDDI and continue as described. If not, the device remains in FIDDI for the next cycle, delivers the ventricular support pace and then mode switches to DDD as discussed.

Thus, the present embodiment provides a protocol by which FIDDI is employed in conjunction with mode switching to DDD to manage ventricular pacing. In summary, the device will switch to DDD for at least one cycle subsequent to a cycle of FIDDI wherein a support pace is delivered. The device will then periodically check for intrinsic conduction and switch to FIDDI if found, remain in DDD if it is determined that conduction checks should not be performed, or switch to FIDDI if intrinsic conduction occurs at a higher rate than the paced rate.

In another embodiment, FIDDI is used in conjunction with the mode supervisor to minimize or reduce ventricular pacing. In general, in this embodiment the device operates in FIDDI and the mode supervisor monitors, as one of its functions, patterns of ventricular pacing and intrinsic ventricular conduction. Thus, in FIDDI a missed ventricular beat is tolerated, the next cycle is paced, and the subsequent cycle allows the full A-A interval to be sensed for ventricular activity. That is, rather than mode switching to DDD after a cycle where FIDDI delivers a ventricular pace, this embodiment remains in FIDDI even after a cycle where ventricular pacing is delivered. The mode supervisor monitors ventricular activity and will cause a mode switch if certain other parameters are met. For example, the mode supervisor will keep the device in FIDDI if there was ventricular activity in three of the last four cardiac cycles. Conversely, if there was ventricular activity in less than three of the last four cardiac cycles, the mode supervisor will trigger a mode switch to, for example, DDD. Various other patterns or parameters can be used to define when the mode switch will occur.

Thus, the mode supervisor can monitor any number of parameters and variables and trigger a mode switch when required. Such variables and parameters can be adjusted over time and/or based on sensed conditions. This allows the device to remain in FIDDI and tolerate a number of missed ventricular beats rather than immediately mode switching whenever there is a missed ventricular beat. Such intermittent missed ventricular beats are often normal and generally harmless. By tolerating these events, the present embodiment further reduces ventricular pacing. The mode supervisor monitors patterns that are indicative of problematic conditions and triggers mode switching as appropriate. Many such problematic conditions are transient or temporary and the mode supervisor can initiate conduction checks and return the device to FIDDI as appropriate. In addition, certain conditions worsen over time. Thus, the mode supervisor can adjust its criteria over time. For example, the mode supervisor may initially be more tolerant of, e.g., the number of missed ventricular beats out of a given number of cycles, prior to mode switching. If, over time, the mode supervisor recognizes patterns that indicate a worsening condition, the parameters can be adjusted to be less tolerant of the number of missed ventricular beats and hence, mode switch accordingly.

Figure 14:
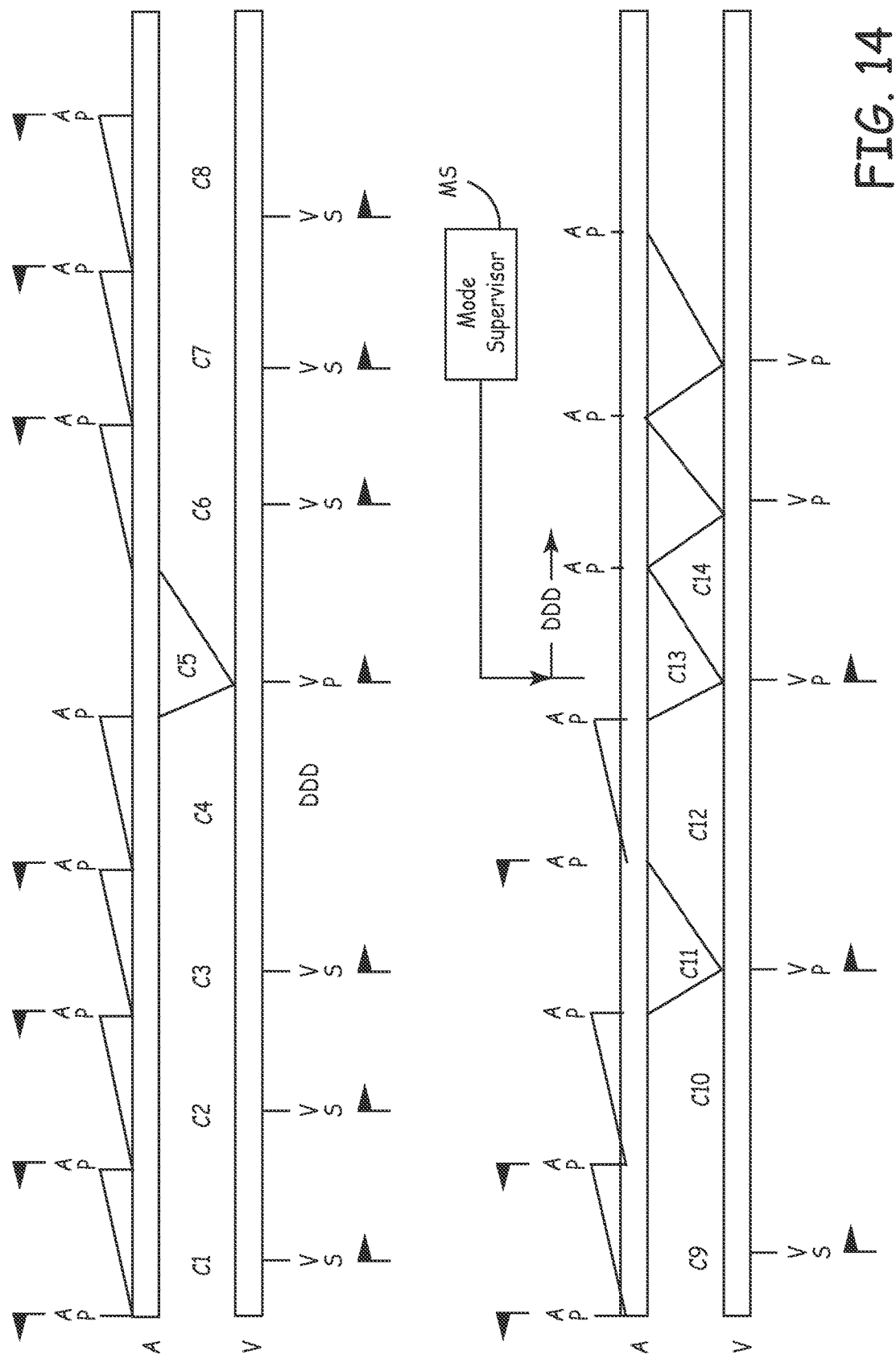

The operation of this embodiment is illustrated with the ladder diagram of FIG. 14. Initially, the device is operating in the FIDDI mode and in cardiac cycles C1-C3, there are normal intrinsic ventricular depolarizations. In cycle C4 there is no ventricular sense (hence a missed ventricular beat) and therefore in cycle C5, FIDDI delivers a ventricular support pace. It should be noted that the device continues to operate in FIDDI. In cycles C6-C9, the appropriate ventricular activity is sensed.

A missed ventricular beat occurs during cycle C10 and during cycle C11, FIDDI delivers the ventricular support pace. During the next cycle, C12, there is another missed ventricular beat. FIDDI monitors the A-A interval of cycle C12 and upon completion, begins the AV interval for cycle C13 and then delivers the support pace. Thus, the device continues to operate in FIDDI until this cycle. However, the mode supervisor determines that a mode switch to DDD is appropriate and the same is affected for cycle C14. For example, the criteria employed could be to remain in FIDDI so long as three of the previous four cardiac cycles included ventricular activity. In the illustrated example, less than three cycles included ventricular activity and the mode switch is performed.

Subsequent to the mode supervisor triggering the mode switch to DDD, various options exist. For example, the device may remain in DDD or periodic conduction checks can be performed and if successful, the mode supervisor will cause the device to mode switch to FIDDI.

As described herein, FIDDI is a complete and independent pacing mode. FIDDI may be used in its base form as a pacing regime, may be used in combination with a mode switching protocol or a mode supervisor to manage ventricular pacing, may be used in combination with other parameters for various therapies, may be used for ventricular rate-halving, or may be used to conduct threshold testing.

U.S. Pat. No. 5,954,755, issued to Casavant on Sep. 21, 1999 and assigned to Medtronic, Inc. discloses a facilitated atrial pacing threshold test (FAPTT) and is herein incorporated by reference in its entirety. FIDDI can be used to implement FAPTT. As a very generalized and simplified overview, FAPTT provides for threshold testing in at least two ways. First, where there is intact AV conduction, the device paces in ADI mode until there is a loss of capture indicated by the absence of a ventricular sense. When that occurs, the device mode switches to DDI and delivers a support pace. The device then mode switches back to ADI to continue the threshold test, either by verifying loss of capture at that level or readjusting the atrial pacing threshold.

Where there is complete block and the patient is pacemaker dependant with ventricular pacing, FAPTT is used to unclutter a resultant EKG. That is, for the pacing threshold test the atrial rate is driven relatively high (e.g., 90-200 bpm). It would be undesirable to have the ventricular rate track this higher rate. If the ventricular rate did track, a resultant, standard EKG would be very crowded and difficult to interpret. Thus, FAPTT mode switches with every single beat between ADI and DDI or vice versa. Each cycle of ADI is devoid of ventricular activity; hence, the resultant EKG is easier to interpret. The ventricular rate is effectively halved compared to the atrial rate, but since the atrial rate is set high for testing, the ventricular rate is ultimately normal. The threshold test is conducted by monitoring for loss of capture in the atrium via the EKG or other means.

In either implementation, FAPTT is simply a threshold test performed for a very limited time and generally under direct supervision of a medical caregiver. FIDDI as a pacing mode can be used to conduct the threshold testing via the FAPTT protocol. That is, FIDDI fully facilitates intrinsic AV conduction and will only deliver a ventricular pace if the previous cycle is devoid of ventricular activity. Thus, by using FIDDI while adjusting atrial thresholds, loss of capture can be identified by a loss of ventricular activity when the patient has otherwise good conduction and the test does not require mode switching. Conversely, when there is complete AV block, FIDDI can be used while setting the atrial rate to a higher rate. Every other beat will be devoid of ventricular activity without requiring a mode switch. Thus, the threshold test can be readily performed without a cluttered EKG and the inherent problems of such frequent mode switching.

Figure 15:
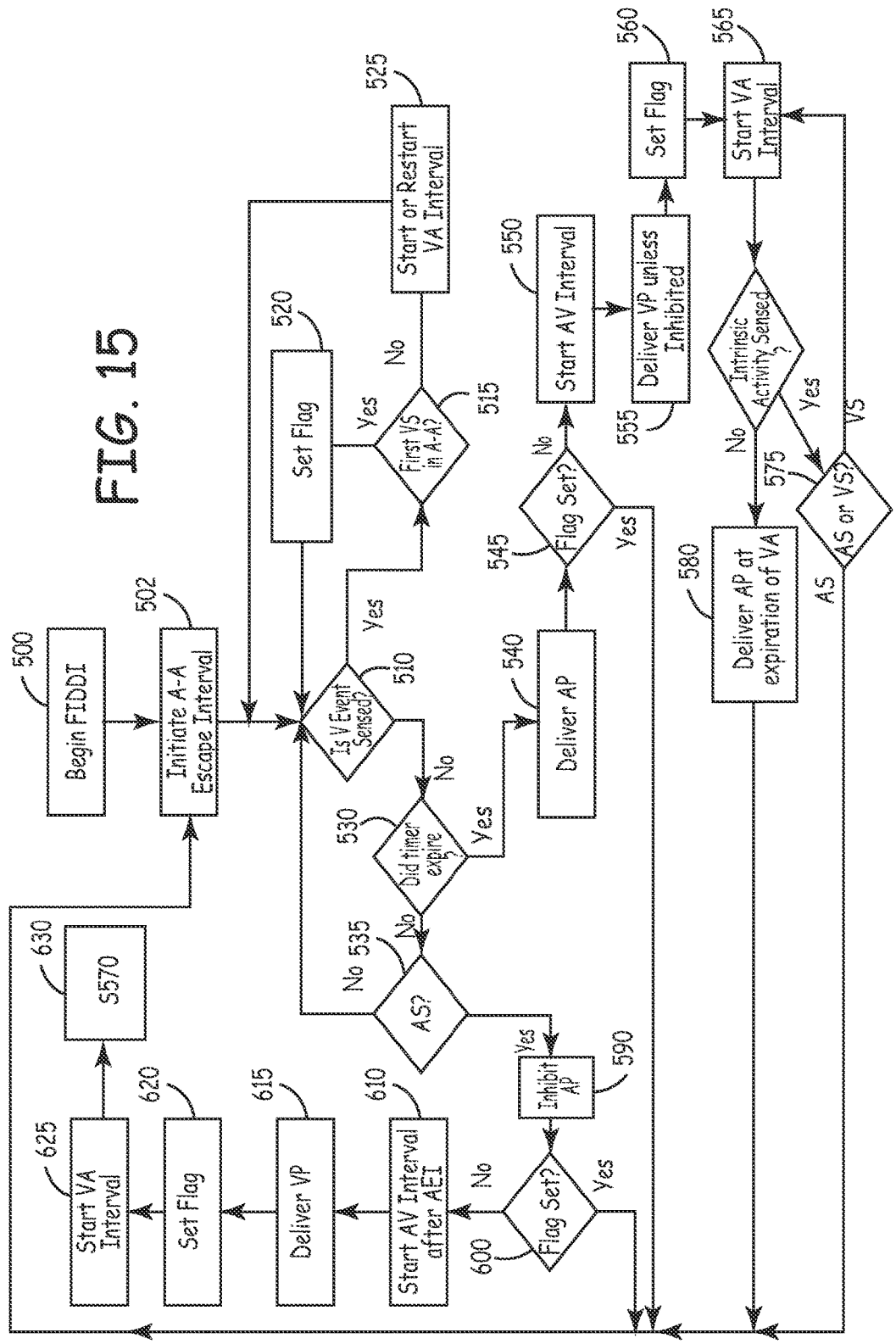
FIG. 15 is a flowchart illustrating a process for implementing the FIDDI mode. 7

FIG. 15 is flowchart that illustrates the FIDDI modality. At some point in time, the device begins operation in FIDDI (S500). Generally, this will occur with a ventricular event that is paced or sensed while the device is in another mode. During that last cycle in the other mode, the device mode switches to FIDDI and the ventricular event sets the flag for the next cycle due. Alternatively, FIDDI could be initiated with an atrial event wherein a flag for that cycle is assumed or the first cycle may be paced by default. In either case, for the first full cycle of operation in FIDDI a flag is set.

After the initiation of FIDDI (S500), the flag is present for the first full cycle of operation in FIDDI and an AEI is initiated (S505) with an atrial pacing pulse or atrial sensed event, if present. As the AEI progresses, the device monitors (S510) for ventricular activity. If there is a ventricular sense, the device determines (S515) if it is the first ventricular sense in the current A-A interval. If it is, the device sets (S520) a flag and continues to monitor (510) until the AEI expires. If the sensed ventricular event was the second or subsequent ventricular sense in the current A-A interval, a VA interval is started (525) or restarted (see e.g., FIG. 12A). This will effectively prolong or elongate the AEI, though the timing is now driven by the VA interval.

The current A-A interval will expire either because the AEI has run, the VA interval has run, or an atrial sense occurs. If the current timer (AEI or VA) has not expired (S530) and there was no atrial sense (S535), the process continues to monitor for ventricular activity (S510).

If the current timer has expired (S530) an atrial pace is delivered (S540). For purposes of this illustration, timer expiration (S530) means that it expired without a sensed atrial event. If there was in fact a sensed atrial event (S535), the process proceeds in a different manner as explained below, regardless of whether the timer actually continues to run or is terminated.

As the AP is delivered (S540), the device determines if there was a flag set (S545). If there was a flag set, the process returns to S505 and the next AEI is initiated. If no flag was set (S545), then the programmed AV (PAV) interval is started (S550). In one embodiment, the PAV is relatively short (e.g., 80 ms) so as to deliver the support pace, but may be programmed to any desired interval. When the PAV expires, the ventricular pace (VP) is delivered (S555). If an intrinsic ventricular event were sensed, the modality would inhibit this ventricular pace. In either case, as a result of the ventricular activity, a flag is set (S560) and the VA interval is started (S565). During this time, the device monitors (S570) for any intrinsic activity and determines (S575) if it is atrial or ventricular. If it is an atrial event, the process then returns to S505 and the next AEI is initiated. If there is a ventricular sense during the VA interval, the VA interval is restarted (S565). If the VA interval expires without interruption, an AP is delivered (580) and the process returns to S505 where the next AEI is initiated.

Returning to S530, if the current timer (AEI or VA) is terminated or interrupted because of an atrial sense (S535), the scheduled AP is inhibited (S590) and the device determines if a flag has been set (S600). If a flag is present (S600), then the process returns to S505 with the initiation of the next AEI. If there was not a flag set (S600), then the programmed AV interval (PAV) is initiated (S610). In this embodiment, the initiation of the PAV is delayed. In practice, the previous AEI (interrupted by the intrinsic atrial activity) is allowed to run and at its expiration, the PAV is initiated. In alternative embodiments, the PAV is initiated with the sensed atrial activity. When the PAV expires, a VP is delivered (S615) (unless inhibited) and a flag is set (S620) for the next cycle. The ventricular activity initiates (S625) a VA interval, during which the device monitors for additional ventricular events (S630). The process then proceeds to S570 and continues as previously described.

At steps S545 and S600 a determination is made as to whether a flag was previously set. In both instances, if a flag is present the process returns to S505 and an AEI is initiated. The flag that was valid at both of these steps does not carry through into the next cycle. Thus, flag may be cleared from memory. Though not illustrated, this may occur after S545 and S600 or may occur with or immediately after S505. Alternatively, rather than clearing the flag from memory, each flag could be correlated with a given interval and thus, would only be valid for that interval.

Throughout this specification various terms have been used to indicate pacing modalities, including designations according to the NBG Pacemaker Code. The use of such terminology is for illustrative purposes only and should not be taken as limiting. These codes, used in the present context, can only approximate the characteristics, rules and functions of the modes that are described. For example, in one embodiment described herein to reduce or minimize pacing, the operation is described as operating in an AAI mode and then mode switching to a DDI mode under certain circumstances. It should be appreciated, for example, that AAI/R, ADI, or ADI/R also describe the relevant operation of the device rather than AAI and are therefore interchangeable. As used herein, "atrial based pacing" mode or modality is used to describe any of these modes (AAI, AAI/R, ADI, ADI/R) and their variants.

Rate responsiveness, while not discussed extensively, is applicable to any of the modalities discussed, including FIDDI. Thus, any modality discussed or approximated may be interchanged with a rate responsive variant without departing from the scope of the present invention.

The modes discussed may be embodied in hardware, firmware, software, code, instructions, or any appropriate format stored in memory or any computer readable medium accessible by the appropriate medical device. The modalities may be incorporated into a device by design or manufacture or may be added to a preexisting device.

Although the present invention has been described with reference to preferred embodiments, persons skilled in the art will recognize that changes may be made in form and detail without departing from the spirit and scope of the invention.

The invention claimed is:
1. A method of selectively providing cardiac pacing with an implantable medical device comprising:
  detecting, via an electrode, ventricular activity during a given cardiac cycle;
  setting, via a processor, a flag during the given cardiac cycle when ventricular activity is detected during the given cardiac cycle;
  determining the flag is set at an onset of a current cardiac cycle, the current cardiac cycle occurring after the given cardiac cycle;

precluding a ventricular pacing pulse during an entirety of the current cardiac cycle when the flag is set at the onset of the current cardiac cycle; and wherein the given and the current cardiac cycles are each initiated by an atrial event and extend only until a next subsequent atrial event.

2. The method of claim 1, wherein the flag is valid only for a cardiac cycle immediately succeeding the given cycle.

3. The method of claim 1, wherein the flag is valid only for one cardiac cycle subsequent to the given cardiac cycle.

4. The method of claim 1 wherein the ventricular activity may occur at any time during the given cardiac cycle to set the flag.

5. A method of selectively providing cardiac pacing with an implantable medical device comprising:

detecting, via an electrode, ventricular activity during a given cardiac cycle;

setting, via a processor, a flag during the given cardiac cycle when ventricular activity is detected during the given cardiac cycle; and determining the flag is set at an onset of a current cardiac cycle, the current cardiac cycle occurring after the given cardiac cycle;

precluding a ventricular pacing pulse during an entirety of the current cardiac cycle when the flag is set at the onset of the current cardiac cycle; and further comprising initiating an atrial escape interval at a start of the current cardiac cycle when the flag is set at the onset of the current cardiac cycle; and wherein the given and the current cardiac cycles are each initiated by an atrial event and extend only until a next subsequent atrial event.

6. The method of claim 5, further comprising:
delivering an atrial pacing pulse at the initiation of the atrial escape interval.

7. The method of claim 6, wherein an intrinsic atrial depolarization initiates the atrial escape interval.

8. The method of claim 7, wherein a scheduled atrial pacing pulse is inhibited.

9. A method of selectively providing cardiac pacing with an implantable medical device comprising:

detecting, via an electrode, ventricular activity during a given cardiac cycle;

setting, via a processor, a flag during the given cardiac cycle when ventricular activity is detected during the given cardiac cycle; and precluding a ventricular pacing pulse during an entirety current cardiac cycle when the flag is set at the onset of the current cardiac cycle;

wherein the given and the current cardiac cycles are each initiated by an atrial event and extend only until a next subsequent atrial event; and further comprising:

initiating an AV interval if, at the onset of the current cardiac cycle, the flag is absent;

delivering a ventricular pacing pulse at the expiration of the AV interval; setting the flag for a subsequent cardiac cycle; and initiating a VA interval with the delivered ventricular pace.

10. The method of claim 9, further comprising:
restarting the VA interval if ventricular activity is sensed during the VA interval.

11. The method of claim 9, further comprising: mode switching to a dual chamber mode for at least one cardiac cycle subsequent to delivering the ventricular pacing pulse.

\* \* \* \* \*